US009959507B2

(12) United States Patent
Mathur et al.

(10) Patent No.: US 9,959,507 B2
(45) Date of Patent: May 1, 2018

(54) PRECISION AGRICULTURE SYSTEM

(71) Applicant: Accenture Global Services Limited, Dublin (IE)

(72) Inventors: Ankur Mathur, Chicago, IL (US); Paul M. Barsamian, Glenview, IL (US); Daniel P. Garrison, Washington, MI (US); Pramila Mullan, Los Gatos, CA (US); Juan C. Mendez, Weston, FL (US)

(73) Assignee: Accenture Global Services Limited, Dublin (IE)

( * ) Notice: Subject to any disclaimer, the term of this patent is extended or adjusted under 35 U.S.C. 154(b) by 0 days. days.

(21) Appl. No.: 15/149,888

(22) Filed: May 9, 2016

(65) Prior Publication Data

US 2016/0253595 A1 Sep. 1, 2016

Related U.S. Application Data

(63) Continuation of application No. 14/663,989, filed on Mar. 20, 2015, now Pat. No. 9,792,557.
(Continued)

(51) Int. Cl.
*G06Q 50/02* (2012.01)
*G01N 33/00* (2006.01)
(Continued)

(52) U.S. Cl.
CPC .............. *G06N 7/005* (2013.01); *A01G 1/001* (2013.01); *G01N 33/0098* (2013.01); *G01N 33/24* (2013.01); *G06F 17/50* (2013.01); *G06N 99/005* (2013.01); *G06Q 50/02* (2013.01); *A01C 7/00* (2013.01); *A01C 15/00* (2013.01);
(Continued)

(58) Field of Classification Search
CPC .... G06Q 50/02; G01N 33/0098; G01N 33/24; A01G 1/001; A01G 25/00; G06N 99/005; G06N 7/005; G06F 17/50; A01C 7/00; A01C 15/00; A01F 25/16; A01D 41/00
See application file for complete search history.

(56) References Cited

U.S. PATENT DOCUMENTS 5,897,619 A * 4/1999 Hargrove, Jr. ......... A01B 79/00
705/317
6,526,120 B1 2/2003 Gray
(Continued)

FOREIGN PATENT DOCUMENTS

CN 101052147 10/2007

OTHER PUBLICATIONS

Extended European Search Report corresponding to EP 16151175. 3, dated Apr. 4, 2016, 9 pages.
(Continued)

*Primary Examiner* — Regis Betsch
(74) *Attorney, Agent, or Firm* — Harrity & Harrity, LLP

(57) ABSTRACT

A device may receive sensor data from a sensor device located on a particular farm. The device may identify an alert, associated with the particular farm, based on the sensor data and using a model. The model may be created based on imagery data and numeric data relating to a group of farms. The device may determine, using the model, a recommended course of action to address the alert, and provide, to a user device associated with the particular farm, the recommended course of action.

20 Claims, 41 Drawing Sheets

Related U.S. Application Data

(60) Provisional application No. 62/103,415, filed on Jan. 14, 2015.

(51) Int. Cl.

| | | |
|---|---|---|
| *G01N 33/24* | (2006.01) | |
| *A01G 1/00* | (2006.01) | |
| *G06N 99/00* | (2010.01) | |
| *G06F 17/50* | (2006.01) | |
| *G06N 7/00* | (2006.01) | |
| *A01G 25/00* | (2006.01) | |
| *A01F 25/16* | (2006.01) | |
| *A01D 41/00* | (2006.01) | |
| *A01C 15/00* | (2006.01) | |
| *A01C 7/00* | (2006.01) | |

(52) U.S. Cl.
CPC .............. *A01D 41/00* (2013.01); *A01F 25/16* (2013.01); *A01G 25/00* (2013.01)

(56) References Cited

U.S. PATENT DOCUMENTS

| | | |
|---|---|---|
| 9,140,824 B1 | 9/2015 | Mewes |
| 9,201,991 B1 | 12/2015 | Mewes |
| 9,563,848 B1 | 2/2017 | Hunt |
| 2010/0290140 A1 | 11/2010 | Ko |
| 2011/0137547 A1* | 6/2011 | Kwon .................... G01C 11/02 701/532 |
| 2012/0101634 A1 | 4/2012 | Lindores |
| 2012/0101861 A1 | 4/2012 | Lindores |
| 2012/0109614 A1 | 5/2012 | Lindores |
| 2013/0018586 A1 | 1/2013 | Peterson |
| 2014/0012732 A1* | 1/2014 | Lindores .............. A01B 79/005 705/37 |
| 2014/0067745 A1* | 3/2014 | Avey ........................ G06N 5/02 706/46 |
| 2014/0089045 A1 | 3/2014 | Johnson |
| 2014/0358486 A1 | 12/2014 | Osborne |
| 2014/0365083 A1 | 12/2014 | Covely |
| 2014/0379228 A1 | 12/2014 | Batcheller |
| 2015/0254800 A1 | 9/2015 | Johnson |
| 2016/0050840 A1* | 2/2016 | Sauder ................ A01B 79/005 701/3 |
| 2016/0202227 A1 | 7/2016 | Mathur |
| 2016/0217231 A1 | 7/2016 | Mewes |
| 2016/0253595 A1 | 9/2016 | Mathur |
| 2016/0373699 A1* | 12/2016 | Torres ................. G05D 1/0038 |
| 2017/0038749 A1 | 2/2017 | Mewes |
| 2017/0055433 A1 | 3/2017 | Jamison |

OTHER PUBLICATIONS

Pioneer, "Pioneer Field 360 Services," https://www.pioneer.com/home/site/us/programs-services/pioneer-field360/, Feb. 9, 2015, 2 pages.

The Climate Corporation, "The Climate Corporation—Protect and improve your profits," http://www.climate.com/, Feb. 1, 2015, 4 pages.

WinField, "WinField," http://www.winfield.com/, Feb. 8, 2015, 2 pages.

Co-pending U.S. Appl. No. 14/663,989, entitled "Precision Agriculture System", by Mathur et al., filed Mar. 20, 2015, 97 pages, U.S. 2016/0202227.

J. Torres-Sánchez et al., "Multi-temporal mapping of the vegetation fraction in early-season wheat fields using images from UAV", Computers and Electronics in Agriculture, vol. 103, Apr. 1, 2014, 10 pages, XP55386811.

Mills et al., "Integrating GNSS, IMU, and Imagery for Automatic Orthomosaic Generation", 22$^{nd}$ International Meeting of the Satellite Division of the Institute of Navigation, Sep. 25, 2009, 12 pages, XP056010487.

Kastens et al., "Image masking for crop yield forecasting using AVHRR NDVI time series imagery", Remote Sensing of Environment, vol. 99, No. 3, Nov. 30, 2005, 16 pages, XP027794817.

\* cited by examiner

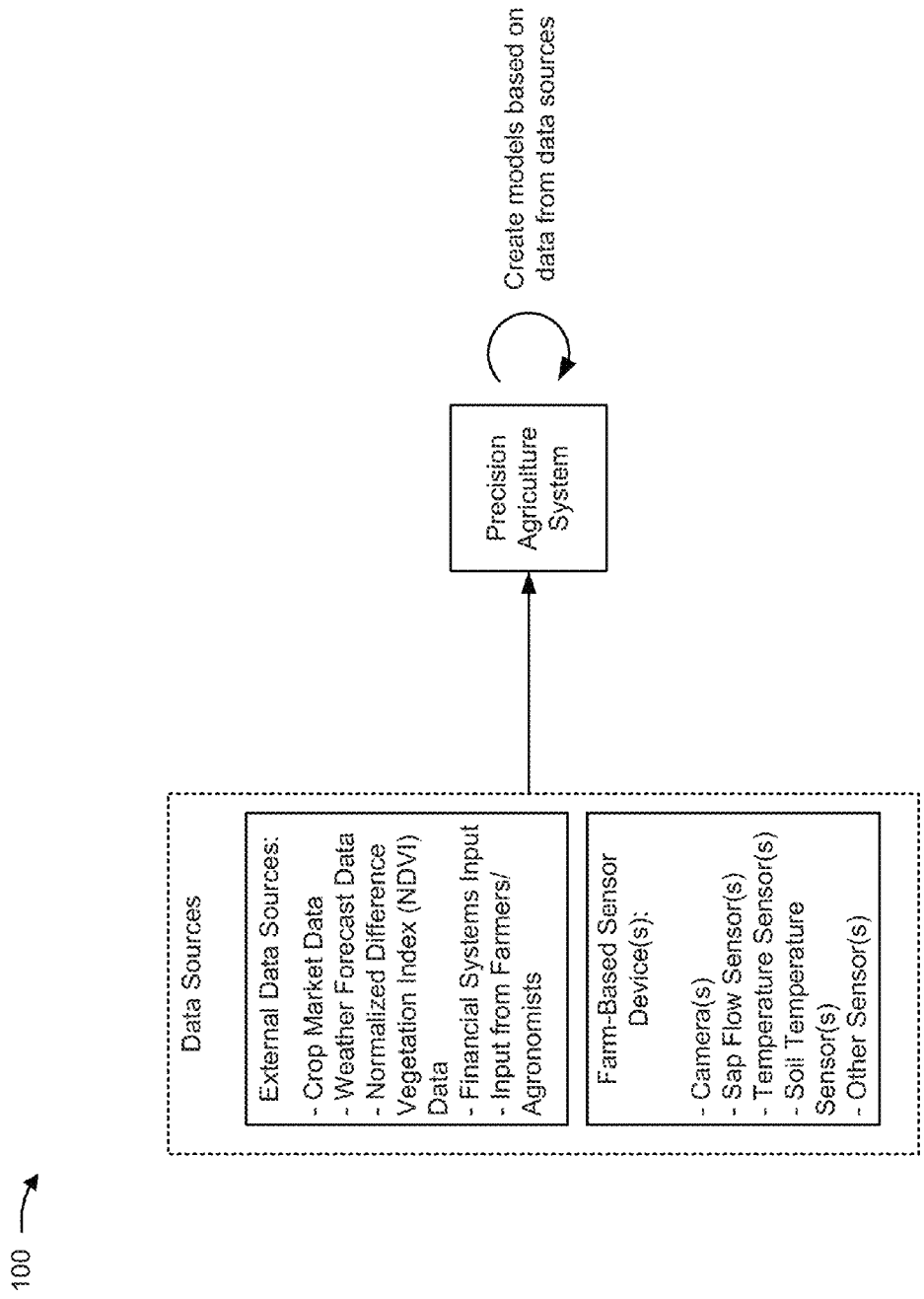

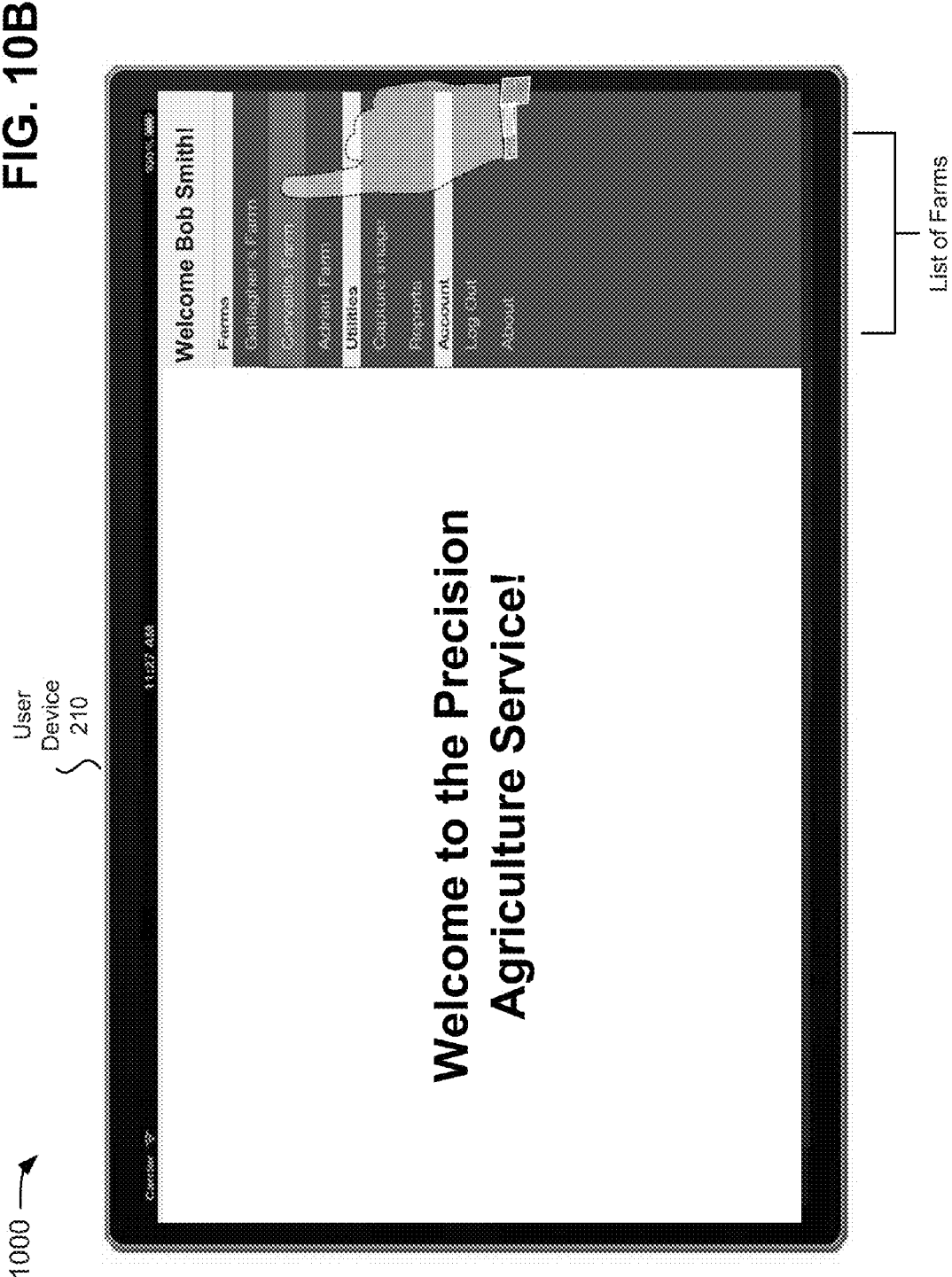

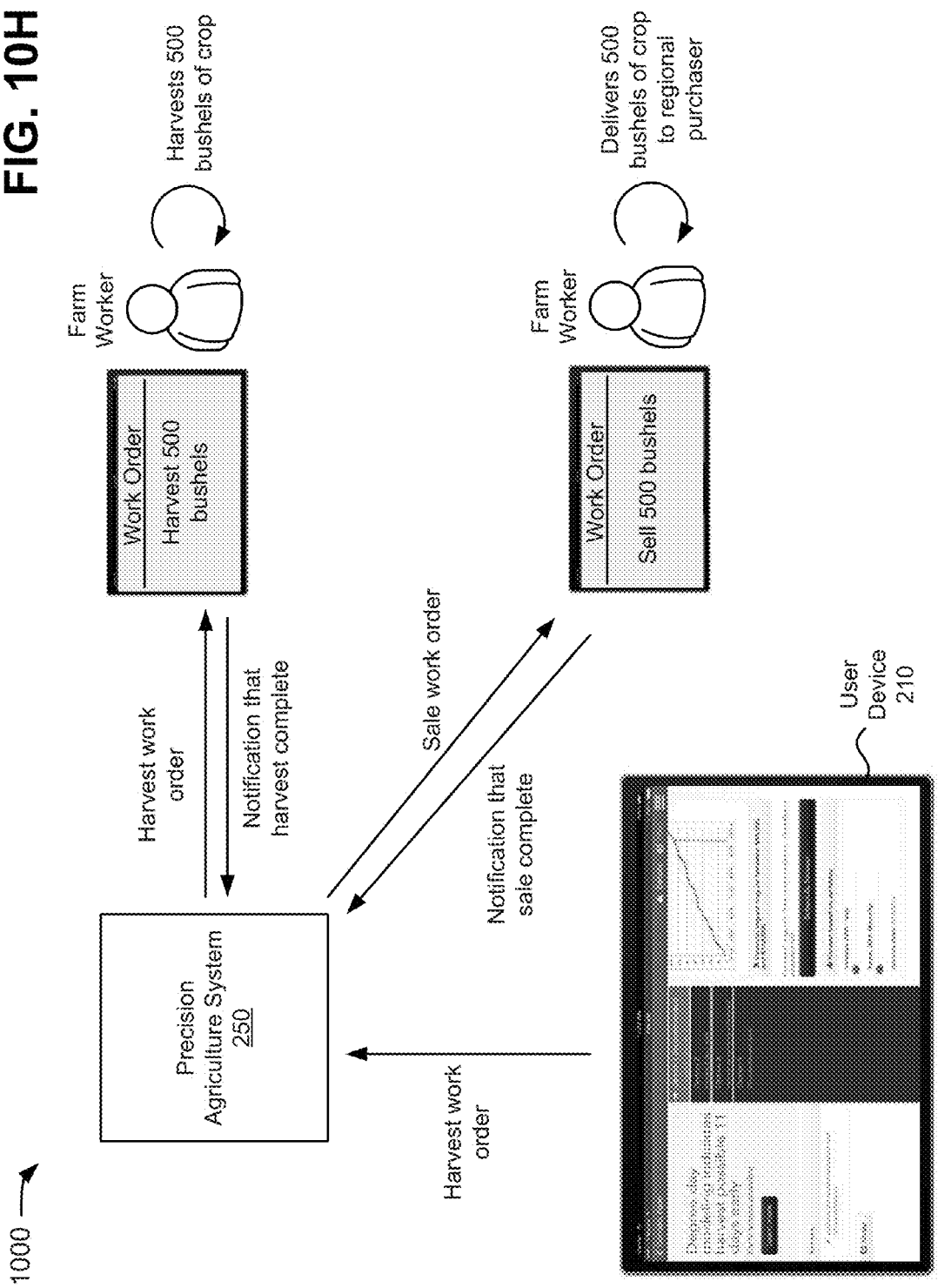

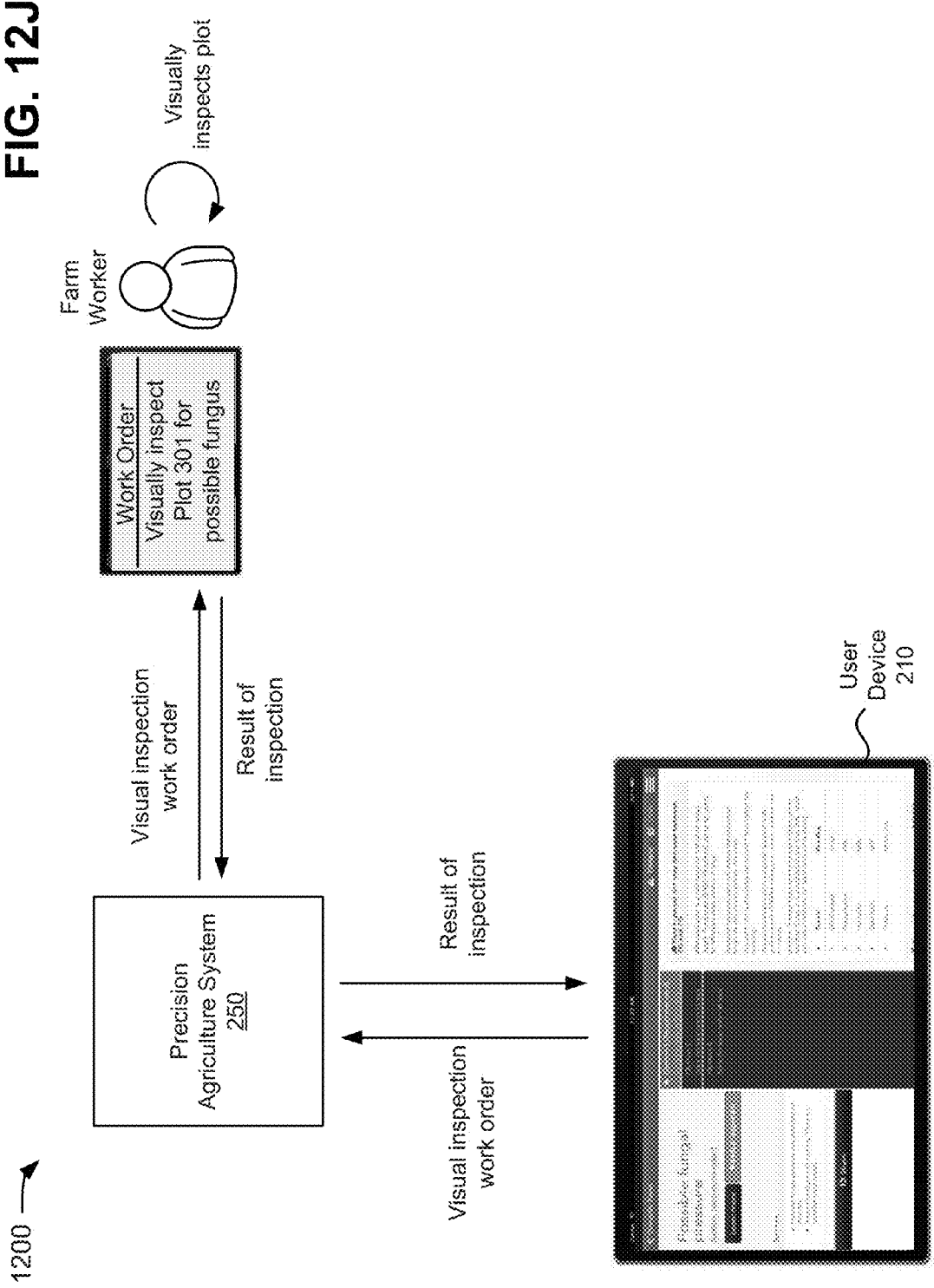

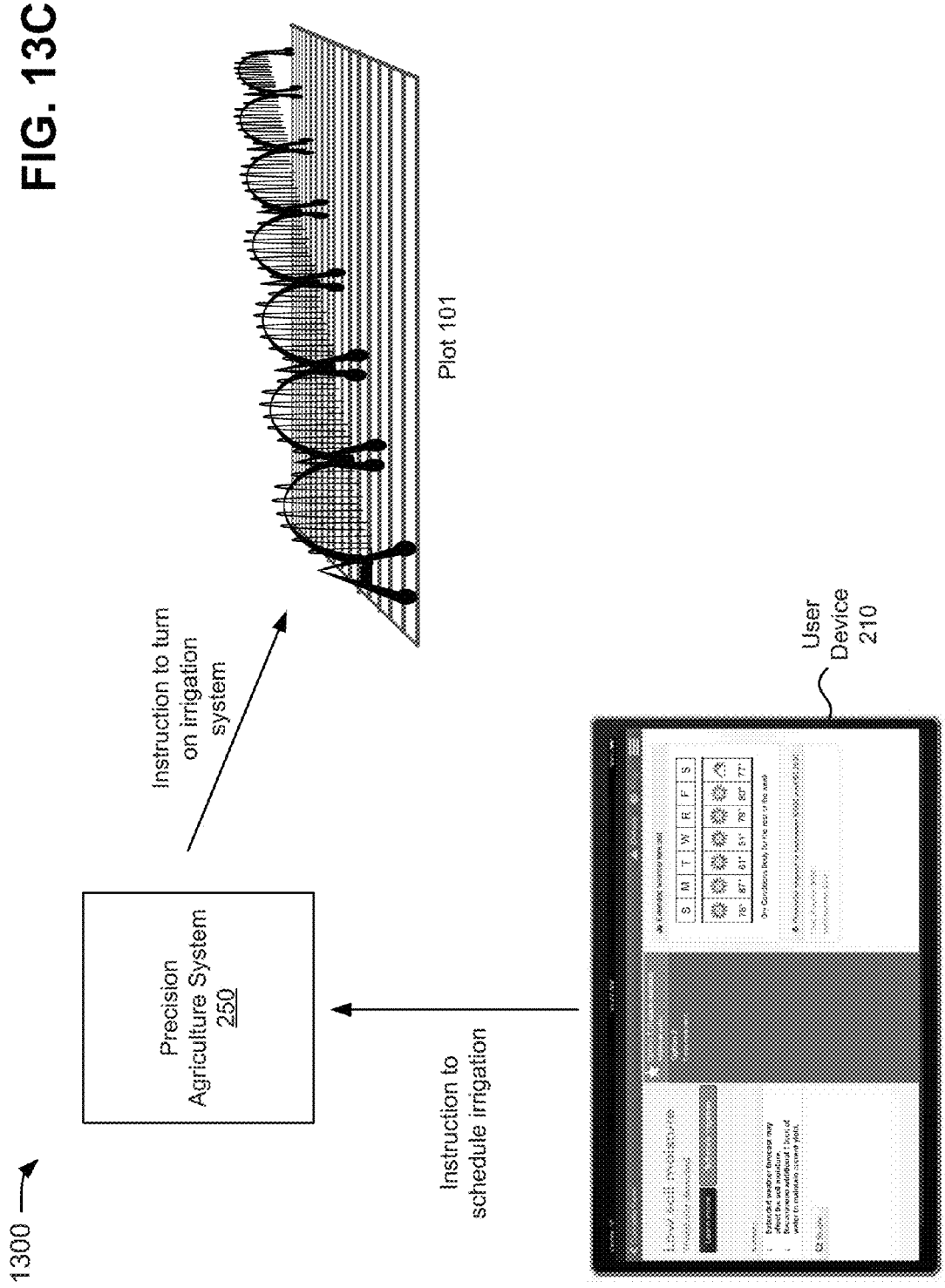

PRECISION AGRICULTURE SYSTEM

RELATED APPLICATIONS

This application is a continuation of U.S. patent application Ser. No. 14/663,989, filed Mar. 20, 2015, which claims priority under 35 U.S.C. § 119 to U.S. Provisional Patent Application No. 62/103,415, filed on Jan. 14, 2015, the contents of which are incorporated by reference herein in their entirety.

BACKGROUND

Today's farmers are faced with many complex issues. For example, today's farmers have to deal with the rising costs of energy, seeds, chemicals, and equipment; variability in weather and climate change, leading to increased unpredictability in crop yields; and environmental pressures on use of chemicals and water.

SUMMARY

According to some possible implementations, a method may include receiving, by a processor of a device, data, the data including first data and second data, the first data being received from a plurality of sensor devices located on one or more farms, and the second data being received from one or more devices located external to the one or more farms; creating, by the processor and using the data, a model; receiving, by the processor, sensor data, the sensor data relating to a particular farm of the one or more farms; identifying, by the processor, an alert, associated with the particular farm, based on the sensor data and using the model; determining, by the processor and using the model, a recommended course of action to address the alert; and providing, by the processor and to a user device associated with the particular farm, the recommended course of action.

According to some possible implementations, a computer-readable medium may store instructions, the instructions including a group of instructions, which, when executed by a processor of a device, cause the processor to receive data, the data including first data and second data, the first data including sensor-related data received from sensor devices located on one or more farms, and the second data including farming-related data received from devices that are located external to the one or more farms; create a model using the data; receive, after creating the model, sensor data, the sensor data being received from a sensor device located on a particular farm; identify an alert, associated with the particular farm, based on the sensor data and using the model; determine, using the model, a recommended course of action to address the alert; and provide, to a user device associated with the particular farm, the recommended course of action.

According to some possible implementations, a device may include a memory to store instructions; and a processor to execute the instructions to receive sensor data, the sensor data being received from a sensor device located on a particular farm; identify an alert, associated with the particular farm, based on the sensor data and using a model, the model being created based on imagery data and numeric data relating to a plurality of farms; determine, using the model, a recommended course of action to address the alert; and provide, to a user device associated with the particular farm, the recommended course of action.

BRIEF DESCRIPTION OF THE DRAWINGS

FIGS. 1A and 1B are diagrams illustrating an overview of an example implementation described herein;

FIGS. 10A-10H are an example of the process described above with respect to FIG. 7;

FIGS. 12A-12L are yet another example of the process described above with respect to FIG. 7; and FIGS. 13A-13C are still another example of the process described above with respect to FIG. 7.

DETAILED DESCRIPTION

The following detailed description refers to the accompanying drawings. The same reference numbers in different drawings may identify the same or similar elements.

A user (e.g., a farmer) may wish to manage a variety of processes related to agriculture (e.g., irrigation, usage of chemicals, crop harvests, etc.). Decision making on a farm is often dependent on an understanding of a variety of factors from information sources that cross a variety of fields. The complexity and quantity of decisions required of a farmer for the successful operation of a farm would benefit from thorough analysis of a large body of shared empirical data. The collection and analysis of this data would be a very time-consuming task for a single farmer. Implementations described herein may aid farmers in running the day-to-day operations of their farms based on information from a variety of sources, such as from sensors on the farm (e.g., that provide information associated with sap flow, imaging, weather, etc.), as well as external sources (e.g., weather forecasts, soil type data, market data, etc.).

Figure 1B:
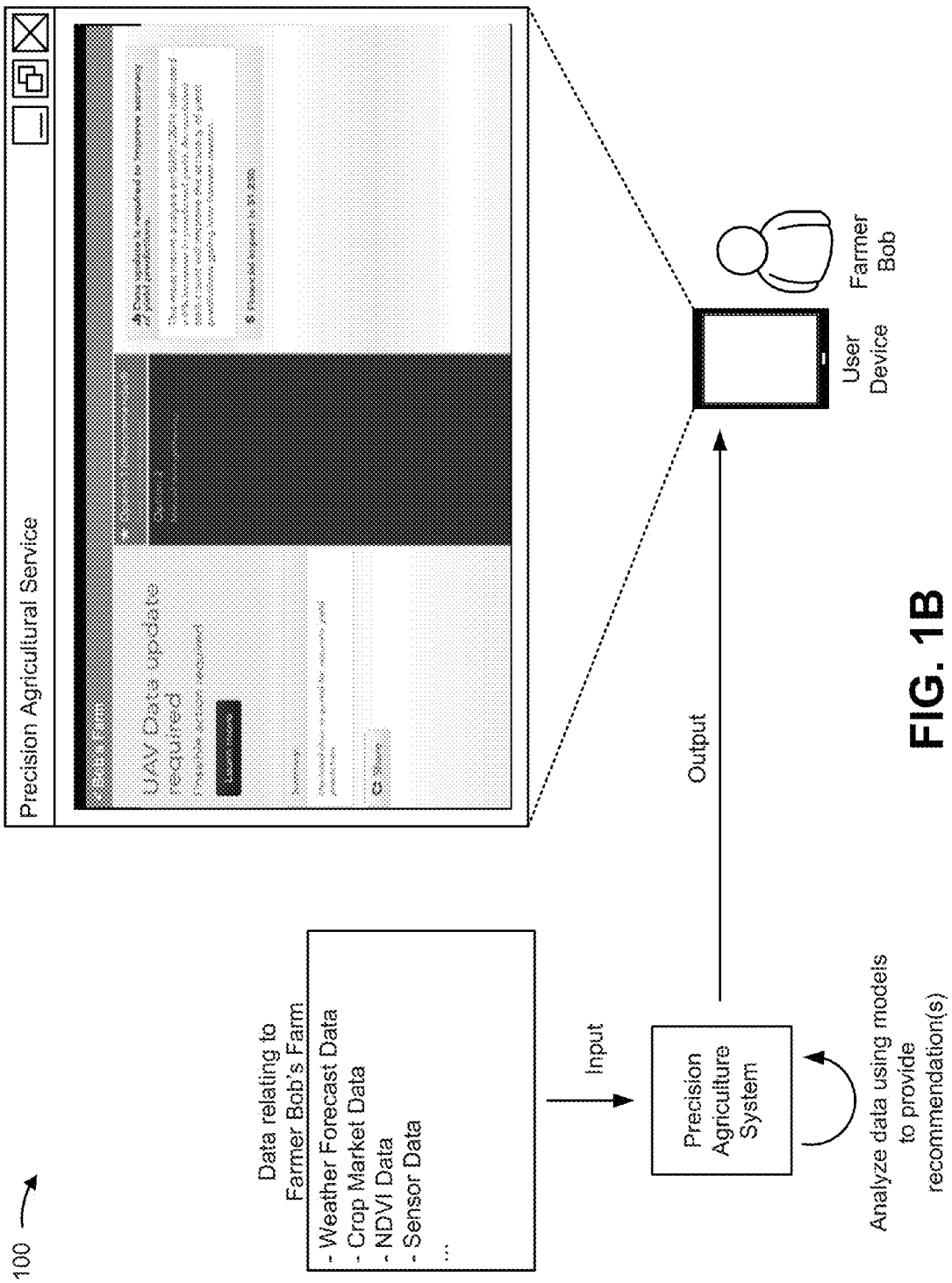

FIGS. 1A and 1B are diagrams illustrating an overview 100 of an example implementation described herein. With reference to FIG. 1A, a precision agriculture system may receive data from a variety of sources and create models based on the received data. The sources of the data may include, for example, farm-based sensor devices and external data sources. The farm-based sensor devices may include cameras, multispectral sensors, sap flow sensors, temperature sensors, soil temperature sensors, ground based or flying drones that gather image data, and/or any other type of sensor device that may aid a farmer in determining how the farmer's crops are doing at any given time. The external data sources may include, for example, crop market data from an external service feed, weather forecast data from a national government or private weather services, cloud based image processing to build crop health indices (e.g., such as Normalized Difference Vegetation Index (NDVI)

images), service feeds that provide financial data relating to crops, input from farmers and/or agronomists, and/or any other external sources of data that may aid in determining rules for making farming decisions.

The precision agriculture system may receive the data from the variety of data sources as a corpus of data, may pre-process the corpus of data to create training data, and may, through the use of machine learning, create one or more models that may be used to identify alerts relating to crops and recommended courses of action. Examples of alerts that may be identified include equipment malfunctions, crops that have patterns of disease or insect infestation, crops that require irrigation, etc. Examples of recommended courses of action may include, a predicted best time to harvest a crop, a predicted best time to sell a crop, the quantity of the crop to sell, when to purchase additional insurance coverage and the amount to purchase, when to water a crop, the quantity of water to use in watering a crop, when to use chemicals (e.g., fungicides) on a crop, the quantity of chemicals to use, when to schedule a worker to perform a particular action, when to schedule a company to repair or perform maintenance on a piece of equipment, etc. The precision agriculture system may also provide, in relation to the identified alerts and/or the recommended courses of action, the financial impact of taking a recommended course of action and/or the financial impact of not taking a recommended course of action.

With reference to FIG. 1B, assume a farmer, named Bob, has registered with the precision agriculture system to use a precision agriculture service. Upon registering, the precision agriculture system may receive data from sensor devices on Bob's farm, as well as from data, relating to Bob's farm, from external data sources. The precision agriculture system may analyze the received data, using the models, to output information relating to Bob's farm. The information may include, for example, weather forecast information, current/scheduled farming activities, alerts relating to Bob's farm, current/historical sensor readings for Bob's farm, commodity prices and trends relevant to Bob's farm, current/historical reports relating to Bob's crops, product inventory and forecasts, and/or any other information that may aid Bob in identifying issues and/or making farming decisions.

As shown, the precision agriculture service has recommended that Bob obtain updated imagery of a particular plot, which has been detected as possibly having an issue, using an unmanned aerial vehicle (UAV). As further shown, the precision agriculture service has indicated a financial impact of $1,250, if the recommended action is not performed.

In this way, the precision agriculture system may provide recommended courses of action, to a farmer, and identify the financial impact of performing and/or not performing the recommended courses of action. A precision agriculture system, as described herein, may reduce operational costs of running a farm, increase crop yields, increase profitability of a farm, reduce risk of crop damage, increase food safety, and reduce a farm's environmental impact.

Figure 2:
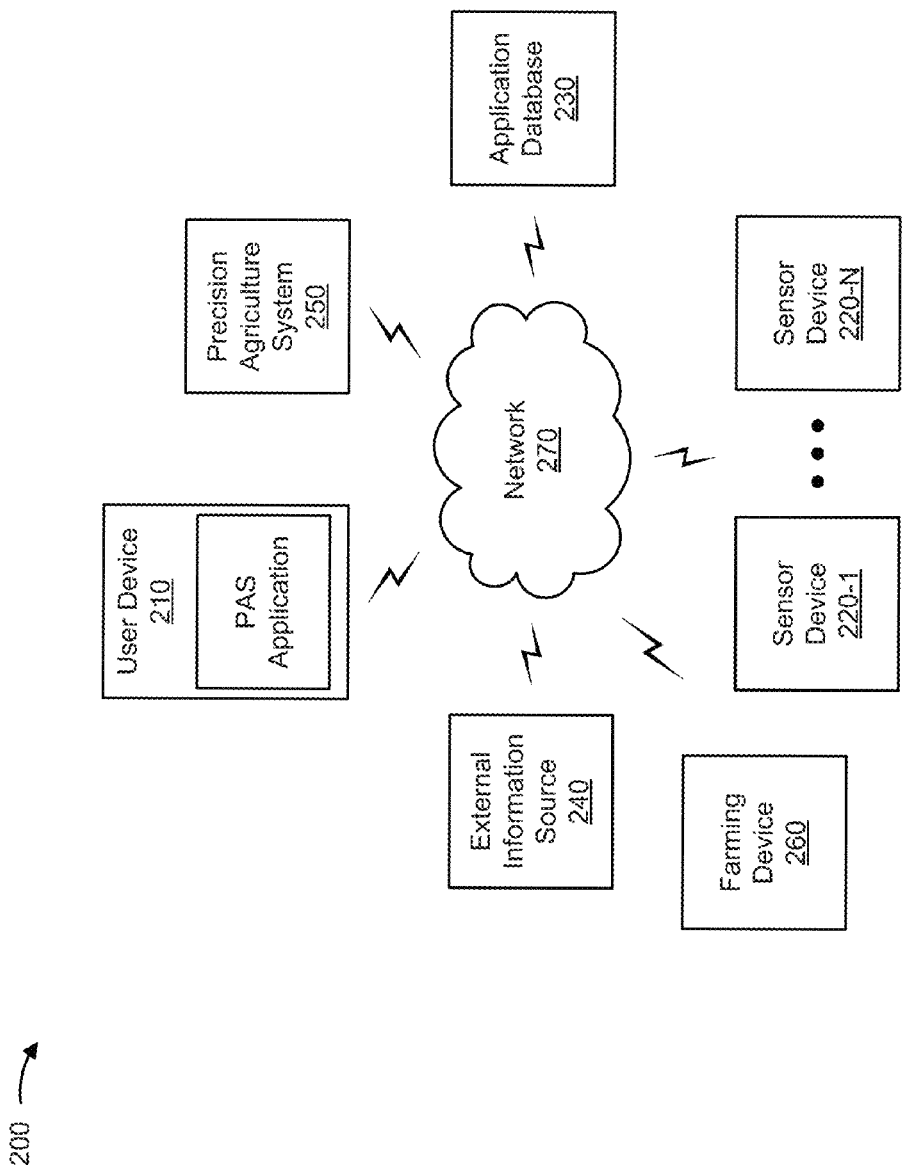
FIG. 2 is a diagram of an example environment in which systems and/or methods described herein may be implemented.

FIG. 2 is a diagram of an example environment 200 in which systems and/or methods described herein may be implemented. As shown in FIG. 2, environment 200 may include a user device 210, one or more sensor devices 220-1 through 220-N (N≥1) (hereinafter referred to collectively as "sensor devices 220," and individually as "sensor device 220"), an application database 230, an external information source 240, a precision agriculture system (PAS) 250, a farming device 260, and a network 270. Devices of environment 200 may interconnect via wired connections, wireless connections, or a combination of wired and wireless connections.

User device 210 may include a device capable of receiving, generating, storing, processing, and/or providing information, such as information described herein. For example, user device 110 may include a computing device (e.g., a desktop computer, a laptop computer, a tablet computer, a handheld computer, a server, etc.), a mobile phone (e.g., a smart phone, a radiotelephone, etc.), or a similar device. In some implementations, user device 210 may receive information from and/or transmit information to precision agriculture system 250. In some implementations, user device 210 may include a Precision Agriculture System (PAS) application that provides information (e.g., sensor information, weather information, aerial imagery, yield projections, financial information, etc.), alerts based on such information, and, if appropriate, action items (e.g., that allow the farmer to initiate automated systems and/or manual operations).

Sensor device 220 may include one or more devices for obtaining sensor-related information. For example, sensor device 220 may include a camera (e.g., a visual spectrum imaging camera, an infrared or near infrared imaging camera, a multispectral imaging camera, a hyperspectral imaging camera, a thermal imaging camera, a laser mapping imagery camera, etc.), a sonar device capable of generating sonar-generated mapping imagery, a sensor capable of detecting precipitation, a sensor capable of detecting sunshine, a sensor capable of detecting relative humidity, a sensor capable of detecting atmospheric pressure, a sensor capable of detecting temperature above ground, a sensor capable of detecting temperature at one or more depths below ground, a sensor capable of detecting wind direction, a sensor capable of detecting wind speed, a sensor capable of detecting rainfall, a sensor capable of detecting irrigation flow, a sensor capable of detecting soil moisture, a sensor capable of detecting soil salinity, a sensor capable of detecting soil density, a sensor capable of detecting sap flow, a sensor capable of detecting equipment operating parameters, a sensor capable of detecting a silo fill level, a sensor capable of detecting a truck fill level, and/or any other sensor that would aid in making operational farming decisions. In some implementations, sensor device 220 may include or be attached to an unmanned aerial vehicle (UAV), an item of farming equipment (e.g., a tractor, an irrigation system, or the like), a tower (e.g., a cell tower or the like), or another type of device/vehicle.

Application database 230 may include one or more devices capable of receiving, generating, storing, processing, and/or providing information, such as information described herein. For example, application database 230 may include a computing device, such as a server, a desktop computer, a laptop computer, a tablet computer, a handheld computer, or a similar device. Application database 230 may store information from a variety of sources and from multiple farms. For example, the information may include information from sensor devices 220 (e.g., field imagery, telemetry, crop growth information, etc.), information from external information source 240 (e.g. weather information, financial market information, etc.), information relating to operations of a farm (e.g., actions taken based on certain sensor readings, whether or not the actions resulted in fixing any identified problems, historical field data, past outcomes, etc.), and/or another type of information that may aid in determining actions to perform in relation to the operation of a farm.

External information source 240 may include one or more devices, accessible through a network, that are sources of information relevant to agricultural decision making. For example, external information source 240 may include a server that provides Doppler weather forecasts, a server that provides satellite imagery, a server that provides vegetation and soil indexes, a server that provides seed/genetic data from manufacturers, a server that provides market data for specific crops, the United States Department of Agriculture (USDA) "soil type" database, a server that provides historical growth trends for particular crops, a device via which a farmer provides best practice information, a device via which an agronomist provides farming-related information, and/or any other type of device that provides information that may aid in determining actions to perform in relation to the operation of a farm.

Precision agriculture system 250 may include one or more devices that translate aggregated data from sensor devices 220 and external information sources 240 into decision support information through the PAS application. For example, precision agriculture system 250 may include one or more server devices, one or more virtual machines, and/or other similar types of devices. In some implementations, precision agriculture system 250 may provide a variety of services, such as image processing and mapping, multi-spectral image analysis, farming data analysis, and/or analysis of financial market trends. Precision agriculture system 250 may also provide machine-to-machine communication interfaces for scheduling and triggering work demands on automated systems (e.g., farming device 260).

In one example, precision agriculture system 250 may determine, based on sensor or weather information that a particular farm plot may be experiencing crop stress. An alert may be generated and presented via the PAS application. An action item may be presented to trigger ground truthing in the affected area, or a fly over by a UAV, to gather imagery for further analysis by precision agriculture system 250. A further action item may be presented to trigger preventative maintenance in the affected area, such as by selective application of fertilizer, or altering irrigation in the affected area.

Farming device 260 may include one or more devices that provide a service at a farm. For example, farming device 260 may include an irrigation system, a tractor, a device associated with soil cultivation (e.g., a cultivator), a device relating to planting (e.g., an air seeder), a device relating to fertilizing (e.g., a fertilizer spreader), a device relating to harvesting (e.g., a harvester), an unmanned aerial vehicle (UAV), a farm worker scheduling system, and/or another similar type of device. In some implementations, farming device 260 may receive information from precision agriculture system 250 and perform an action based on receiving the information. For example, in the situation where farming device 260 is an irrigation system, the irrigation system may receive information from precision agriculture system 250 and water a particular portion of a plot of the farm for a period of time based on the received information.

Network 270 may include one or more wired and/or wireless networks. For example, network 270 may include a cellular network (e.g., a long-term evolution (LTE) network, a 3G network, a code division multiple access (CDMA) network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, a cloud computing network, and/or a combination of these or another type of network.

The number and arrangement of devices and networks shown in FIG. 2 are provided as an example. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. Additionally, or alternatively, a set of devices (e.g., one or more devices) of environment 200 may perform one or more functions described as being performed by another set of devices of environment 200.

Figure 3:
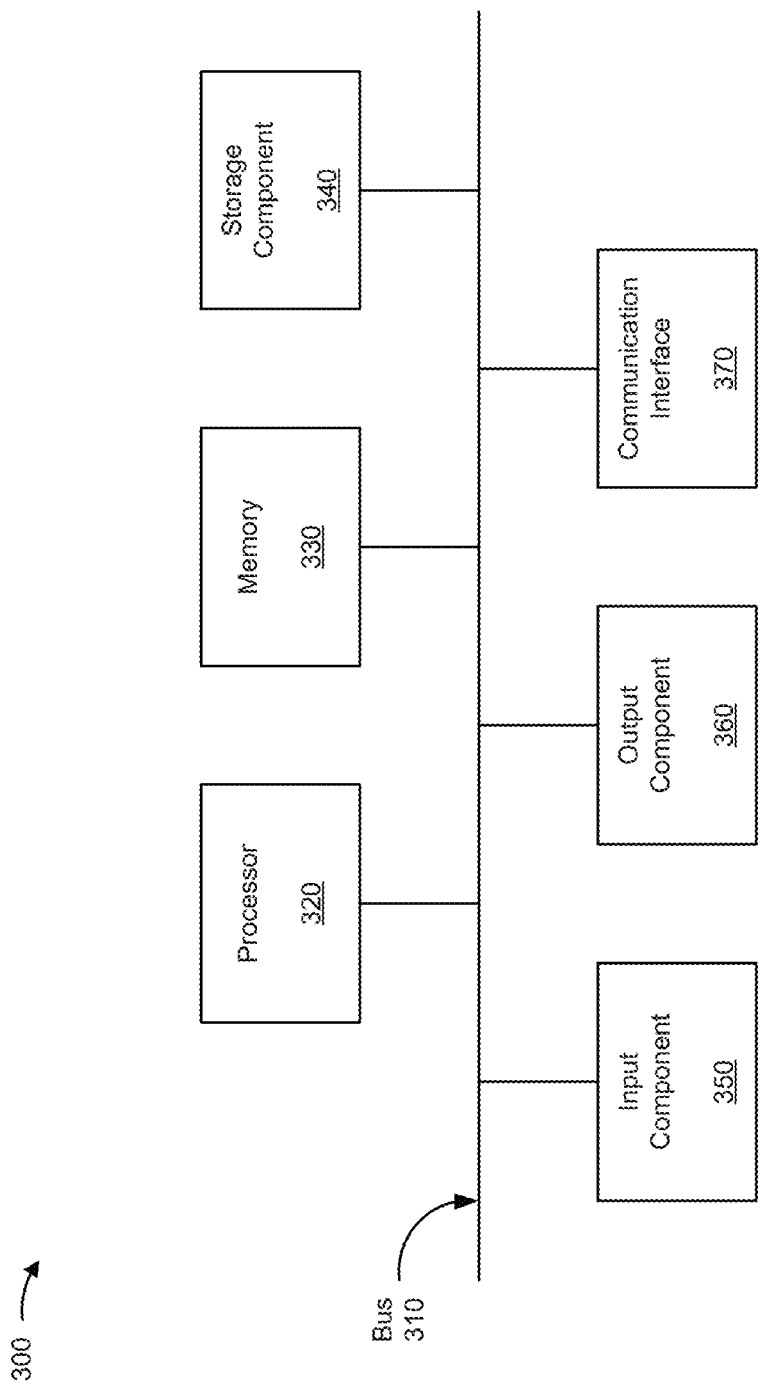
FIG. 3 is a diagram of example components of one or more devices of FIG. 2.

FIG. 3 is a diagram of example components of a device 300. Device 300 may correspond to user device 210, sensor device 220, application database 230, external information source 240, precision agriculture system 250, and/or farm device 260. In some implementations, user device 210, sensor device 220, application database 230, external information source 240, precision agriculture system 250, and/or farm device 260 may include one or more devices 300 and/or one or more components of device 300. As shown in FIG. 3, device 300 may include a bus 310, a processor 320, a memory 330, a storage component 340, an input component 350, an output component 360, and a communication interface 370.

Bus 310 may include a component that permits communication among the components of device 300. Processor 320 is implemented in hardware, firmware, or a combination of hardware and software. Processor 320 may include a processor (e.g., a central processing unit (CPU), a graphics processing unit (GPU), an accelerated processing unit (APU), etc.), a microprocessor, and/or any processing component (e.g., a field-programmable gate array (FPGA), an application-specific integrated circuit (ASIC), etc.) that interprets and/or executes instructions. Memory 330 may include a random access memory (RAM), a read only memory (ROM), and/or another type of dynamic or static storage device (e.g., a flash memory, a magnetic memory, an optical memory, etc.) that stores information and/or instructions for use by processor 320.

Storage component 340 may store information and/or software related to the operation and use of device 300. For example, storage component 340 may include a hard disk (e.g., a magnetic disk, an optical disk, a magneto-optic disk, a solid state disk, etc.), a compact disc (CD), a digital versatile disc (DVD), a floppy disk, a cartridge, a magnetic tape, and/or another type of computer-readable medium, along with a corresponding drive.

Input component 350 may include a component that permits device 300 to receive information, such as via user input (e.g., a touch screen display, a keyboard, a keypad, a mouse, a button, a switch, a microphone, etc.). Additionally, or alternatively, input component 350 may include a sensor for sensing information (e.g., a global positioning system (GPS) component, an accelerometer, a gyroscope, an actuator, etc.). Output component 360 may include a component that provides output information from device 300 (e.g., a display, a speaker, one or more light-emitting diodes (LEDs), etc.).

Communication interface 370 may include a transceiver-like component (e.g., a transceiver, a separate receiver and transmitter, etc.) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, or the like.

Device 300 may perform one or more processes described herein. Device 300 may perform these processes in response to processor 320 executing software instructions stored by a computer-readable medium, such as memory 330 and/or storage component 340. A computer-readable medium is defined herein as a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
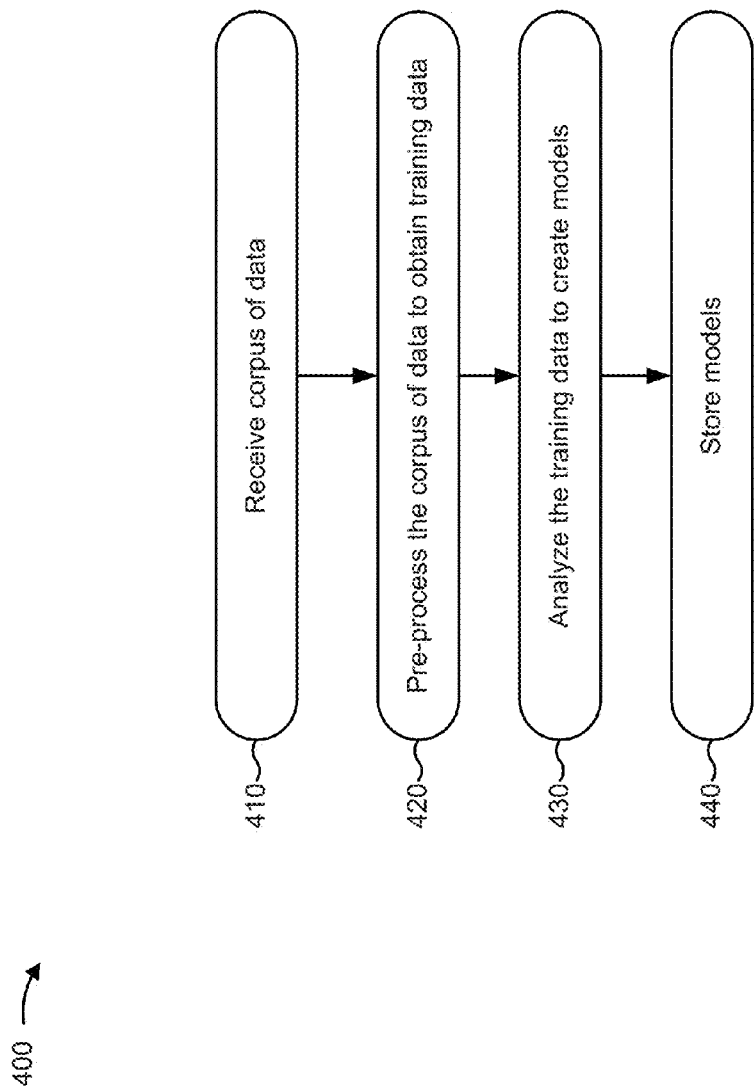
FIG. 4 is a flowchart of an example process for generating and storing models.

FIG. 4 is a flowchart of an example process 400 for generating and storing models. In some implementations, process 400 may be performed by precision agriculture system 250. In some implementations, some or all of the blocks described below may be performed by a different device or group of devices, including or excluding precision agriculture system 250.

As shown in FIG. 4, process 400 may include receiving a corpus of data (block 410). For example, precision agriculture system 250 may receive a corpus of data. The corpus of data may include data from sensor devices 220 and/or external information sources 240. For example, the corpus of data may include data from a camera (e.g., a visual spectrum imaging camera, an infrared or near infrared imaging camera, etc.), a sap flow sensor, a temperature sensor, a soil temperature sensor, a water sensor, a wind sensor, and/or another type of sensor/device located on or near a farm. The corpus of data may also, or alternatively, include data from a server that provides Doppler weather forecasts or historical weather information, a server that provides image data and or agricultural index data from government and/or academic sources, a server that provides market data for specific crops, the USDA "soil type" database, a server that provides historical growth trends for particular crops, farmers (e.g., data relating to best practices for running a farm), agronomists, and/or another source that provides information that may be useful in creating models relating to a farm or group of farms. In some implementations, a piece of data may be associated with information identifying a geographic location to which the data is associated and a date and/or time with which the data is associated. For example, if the data is from a soil temperature sensor, the data may be associated with the geographic location of the soil temperature sensor and the date/time at which the sensor reading occurred.

In some implementations, the data may include imagery data and numeric data, such as an NDVI index or thermal data ranges. The imagery data may include, for example, satellite imagery on the Red/Green/Blue (RGB) spectrum (i.e., each image dot corresponds to a value of red, green, or blue to recreate a color observable by the human eye), satellite imagery on multiple spectral bands (e.g., near infrared (NIR), and/or similar spectral bands), satellite hyperspectral imagery, aerial imagery (e.g., taken by planes, UAVs, etc.) on the RGB, thermal or NIR spectrum, aerial imagery (e.g., taken by planes, UAVs, etc.) on multiple spectral bands, aerial hyperspectral imagery, sonar-generated imagery, geographical features described through coordinates, as boundaries, polygons, or dots, and/or ground-level imagery (e.g., RGB, infrared, thermal, multispectral, hyperspectral, laser, etc.) taken by users, which may be geo-located and uploaded to precision agriculture system 250. The numeric data may include, for example, data relating to precipitation, sunshine, relative humidity, atmospheric pressure, moisture, sap flow, temperature above and below ground, temperature at different depths, wind direction and speed, irrigation flow, equipment operating parameters (e.g., voltage, power outputs, etc.), equipment errors (e.g., radio error rates, delays, etc.), commodity prices (e.g., soy, corn, etc.), and/or fill levels (e.g., of silos, trucks, etc.).

In some implementations, the corpus of data may include current data, historical data, and/or predicted data. For example, the corpus of data may include weather-related information. The weather-related information may include information relating to the current weather, information related to historical weather, and/or information relating to weather forecasts.

In some implementations, precision agriculture system 250 may receive the corpus of data directly from sensor devices 220 and/or external information sources 240. In some implementations, precision agriculture system 250 may receive the corpus of data from application database 230. In either event, the corpus of data may include raw data (e.g., data in various units of measure). In some situations, precision agriculture system 250 may receive data in real time or near real time. In some situations, precision agriculture system 250 may receive data at particular time intervals (e.g., once an hour, once a day, once a week, or the like). In some implementations, precision agriculture system 250 may receive the data passively. In some implementations, precision agriculture system 250 may receive the data based on requesting the data from a particular source (e.g., from a sensor device 220 and/or from an external information source 240).

As further shown in FIG. 4, process 400 may include pre-processing the corpus of data to obtain training data (block 420). For example, precision agriculture system 250 may pre-process the corpus of data to put the data into a format that may be analyzed to create models. In some implementations, precision agriculture system 250 may filter the data in the corpus of data. For example, precision agriculture system 250 may filter the corpus of data to remove unneeded or incorrect data. For example, assume that the data received from an external information source 240 includes weather information for all of the United States. Assume further that precision agriculture system 250 is creating a model for farms in a particular state of the United States. In this event, precision agriculture system 250 may discard weather information for every state, with the exception of the particular state. Similarly, the corpus of data may include satellite imagery for locations around the world and precision agriculture system 250 may filter the imagery to only those locations of interest.

In some implementations, precision agriculture system 250 may normalize the data in the corpus of data. For example, precision agriculture system 250 may convert temperature-related data, in the corpus of data, to ensure that all the temperature-related data is represented in one of Fahrenheit or Celsius.

In some implementations, precision agriculture system 250 may perform one or more other types of processes on the corpus of data to put the data into a format that may be analyzed to create models, such as by combining and/or grouping data. For example, the data may be grouped based on a geographic location with which the data is associated, based on a farm with which the data is associated, based on a date and time with which the data is associated, etc. In addition, As further shown in FIG. 4, process 400 may include analyzing the training data to create models (block 430). For example, precision agriculture system 250 may use machine learning techniques to analyze the training data and create models. The machine learning techniques may include, for example, supervised and/or unsupervised techniques, such as artificial networks, Bayesian statistics, learning automata, Hidden Markov Modeling, linear classifiers, quadratic classifiers, decision trees, association rule learning, or the like. The created models may include models that are specific to a particular farm and models that are generally applicable to all farms.

In some implementations, precision agriculture system 250 may generate more than one model for a particular farm. For example, in some implementations, precision agriculture system 250 may generate one or more models for each plot on the farm. Thus, if a farm is associated with 100 plots, precision agriculture system 250 may generate 100 or more models for the farm. In a situation where a particular plot includes more than one crop, precision agriculture system 250 may generate one or more models for each crop in the particular plot.

As further shown in FIG. 4, process 400 may include storing the models (block 440). For example, precision agriculture system 250 may store the created models in a data structure (e.g., a database, a linked list, a tree, or the like). The data structure may be located within precision agriculture system 250 or external, and possibly remote from, precision agriculture system 250. In some implementations, the data structure may be associated with application database 230.

Once the models have been created, precision agriculture system 250 may further train the models and/or create new models, based on receiving new training data. The new training data may include, in addition to the data discussed above in relation to the corpus of data, data from user devices 210 that are being used by farmers. This data may include information relating to actions taken in particular situations on a farm and the results of those actions. For example, assume that precision agriculture system 250 recommends, to a particular farmer, that a particular chemical be sprayed in a particular plot on the farmer's farm based on data from one or more sensor devices 220 on the farmer's farm. Assume that the spraying occurred and that the farmer indicates, to precision agriculture system 250 and via a user device 210, that the spraying occurred. Assume further that precision agriculture system 250 determines that the issue is not resolved. In this situation, precision agriculture system 250 may update one or more models based on this information.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

Figure 5:
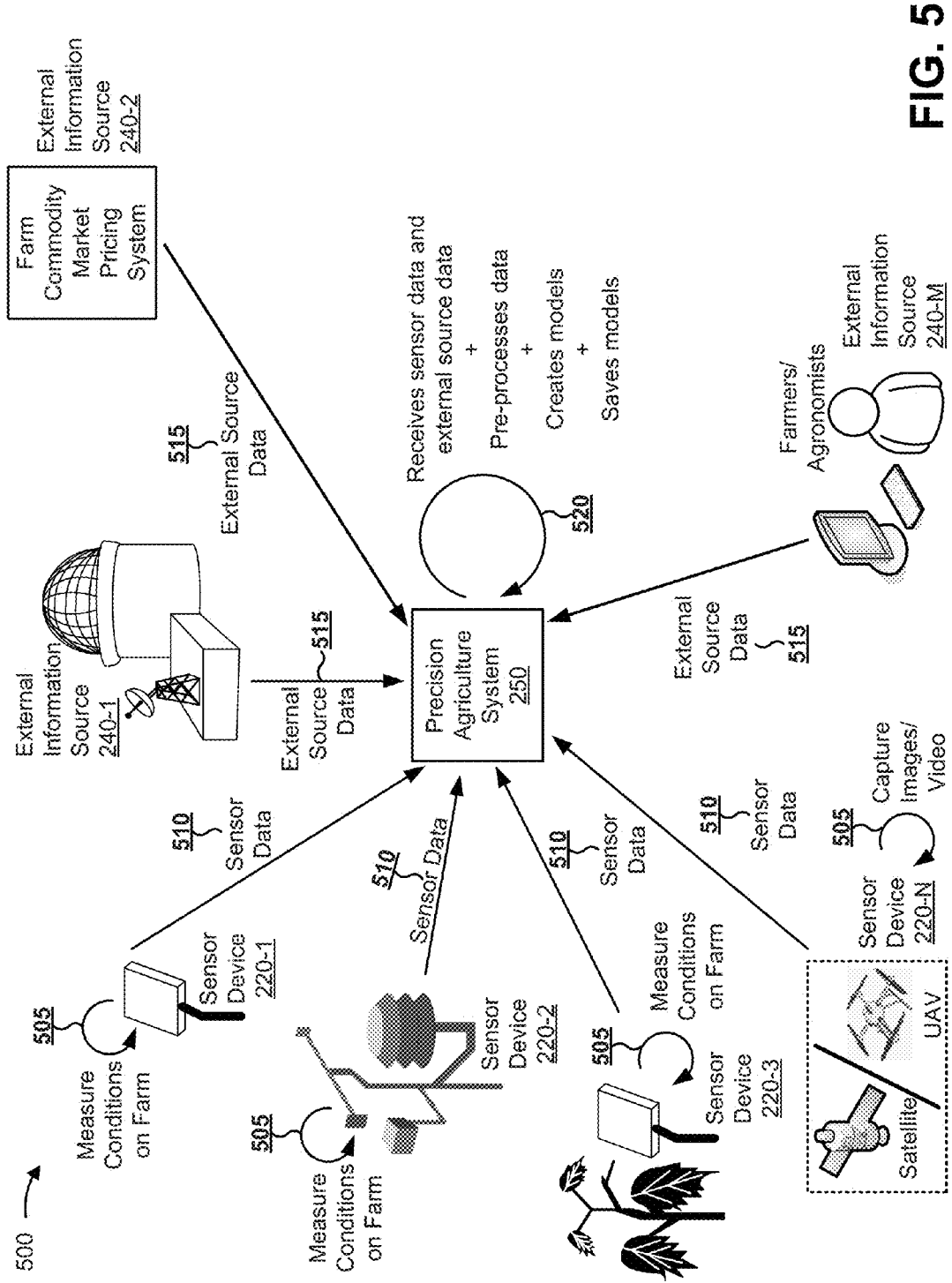
FIG. 5 is a diagram of an example implementation relating to example the process shown in FIG. 4.

FIG. 5 is a diagram of an example implementation 500 relating to example process 400 shown in FIG. 4. As shown by reference number 505, sensor devices 220-1 through 220-N may measure conditions on a farm. Sensor devices 220-1 through 220-N may include, respectively, a temperature sensor, a wind sensor, a sap flow sensor, and imagery devices (shown as a satellite and a UAV). Precision agriculture system 250 may receive sensor data 510 from sensor devices 220-1 through 220-N. In addition, precision agriculture system 250 may receive external source data 215 from a group of external information sources 240-1 through 240-M, shown, respectively, as a weather forecast center, a farm commodity market pricing system, and farmers/agronomists. As shown by reference number 520, precision agriculture system 250 may receive sensor data 510 and external source data 515, pre-process the data to obtain training data, create models based on the training data, and save the models.

As indicated above, FIG. 5 is provided merely as an example. Other examples are possible and may differ from what was described with regard to FIG. 5.

Figure 6:
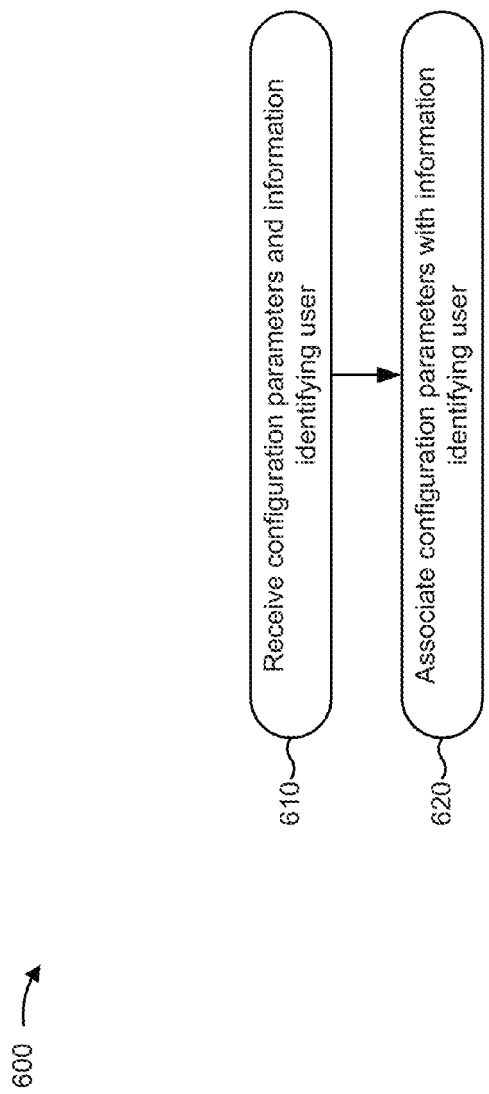
FIG. 6 is a flowchart of an example process for setting configuration parameters for a farmer.

FIG. 6 is a flowchart of an example process 600 for setting configuration parameters for a farmer. In some implementations, one or more blocks of FIG. 6 may be performed by precision agriculture system 250. In some implementations, one or more blocks of FIG. 6 may be performed by a different device or group of devices, including or excluding precision agriculture system 250, such by user device 210, via the PAS application.

As shown in FIG. 6, process 600 may include receiving configuration parameters and information identifying a user (block 610). For example, precision agriculture system 250 may receive one or more configuration parameters from a user (e.g., a farmer). The configuration parameters may include parameters relating to the farmer's farm. For example, the configuration parameters may include information relating to the farm in general, such as the overall size of the farm, the geographic location of the farm, insurance coverage relating to the farm, financial information relating to the farm (e.g., the cost of the land on which the farm is located), historical information relating to the farm (e.g., such as the financial history of the farm), and/or other similar types of information.

The configuration parameters may also, or alternatively, include information relating to the plots on the farm. For each plot, this information may include information identifying a name of the plot, the geographic location of the plot, the size of the plot, the crop(s) with which the plot is associated, financial information relating to the plot, historical information relating to the plot (e.g., such as historical crop yields, a financial history of the plot, etc.), and/or other similar types of information. The configuration parameters may also, or alternatively, include information relating to silos on the farm, such as the name of the silo, the geographic location of the silo, the size of the silo, the type of crop with which the silo is associated, the quantity of the crop in the silo, the remaining capacity of the silo, financial information relating to the silo, historical information relating to the silo (e.g., such as a financial history relating to the crop in the silo), and/or other similar types of information.

The configuration parameters may also, or alternatively, include information relating to machinery on the farm, such as the name of the machinery (e.g., a model number), the type of the machinery, the geographic location of the machinery, information for controlling the machinery (e.g., a network address), a current schedule of operation of the machinery, historical information relating to the machinery (e.g., such as previous maintenance on the machinery, historical schedules of operation of the machinery, etc.), and/or other similar types of information. The configuration parameters may also, or alternatively, include information relating to workers on the farm, such as identification information of the worker (e.g., a name, a numerical identifier, or the like), communication information (e.g., a language that the worker speaks, an email address or phone number for contacting the worker, etc.), the plot(s) with which the worker is typically associated, the worker's current work schedule, historical information relating to the worker (e.g., previous work schedules, salary information, etc.), and/or other similar types of information.

The configuration parameters may also, or alternatively, include information relating to sensor devices 220 on the farm, such as the name of the sensor device (e.g., a model number), the type of the sensor device, the geographic location of the sensor device, information for controlling the sensor device (e.g., a network address), a current schedule of operation of the sensor device, historical information relating to the sensor device (e.g., such as an installation date of the sensor device, previous maintenance on the sensor device, historical schedules of operation of the sensor device, etc.), and/or other similar types of information. The configuration parameters may also, or alternatively, include historical action-related information relating to the farm, such as previous actions taken on the farm and results of those actions.

The configuration parameters may also, or alternatively, include information relating to the type of information to provide and/or a manner in which information is to be provided to user device 210, via the PAS application. The type of information may specify that only particular types of sensor data is to be provided and/or that only particular types of recommendations (or alerts) are to be provided. The manner in which the information is provided may include, for example, an order in which farming-related information and recommendations are to be displayed, a time at which particular pieces of farming-related information and recommendations are to be provided to user device 210, a location, on a user interface, at which particular pieces of the farming-related information and recommendations (or alerts) are to be displayed, and/or other types of information relating to type of information to provide and/or the manner in which information is provided, for display, to user device 210.

In some implementations, precision agriculture system 250 may limit the quantity and type of configuration parameters that can be set by a particular user, based on an account of the user. For example, different users may be associated with different service levels (e.g., a bronze level, a silver level, and a gold level). In these situations, precision agriculture system 250 may restrict the quantity and type of configuration parameters that a user may set based on the service level with which the user is associated.

In some implementations, precision agriculture system 250 may provide a user interface to user device 210 (e.g., to a browser of user device 210) to allow the user to specify the configuration parameters. In some implementations, user device 210 may download an application (e.g., the PAS application) associated with obtaining farming-related information. In these implementations, user device 210 may provide the user interface via the application. In any event, the user may specify the configuration parameters, via the user interface, and may cause the configuration parameters to be sent to precision agriculture system 250.

Precision agriculture system 250 may also receive information identifying the user and/or user device 210. For example, precision agriculture system 250 may provide a user interface to user device 210 to allow the user to specify the identification information. In some implementations, precision agriculture system 250 may receive the identification information via a log in process. In those implementations where user device 210 downloads an application associated with obtaining farming-related information, user device 210 may transmit the identification information using the application.

Process 600 may include associating the configuration parameters with the information identifying the user (block 620). For example, precision agriculture system 250 may store the configuration parameters in a data structure. The data structure may be located within precision agriculture system 250 or external, and possibly remote from, precision agriculture system 250 (e.g., in application database 230). Precision agriculture system 250 may associate the data structure (or that portion of the data structure that stores the configuration parameters) with the information identifying the user and/or user device 210.

Although FIG. 6 shows example blocks of process 600, in some implementations, process 600 may include additional blocks, fewer blocks, different blocks, or differently arranged blocks than those depicted in FIG. 6. Additionally, or alternatively, two or more of the blocks of process 600 may be performed in parallel.

Figure 7:
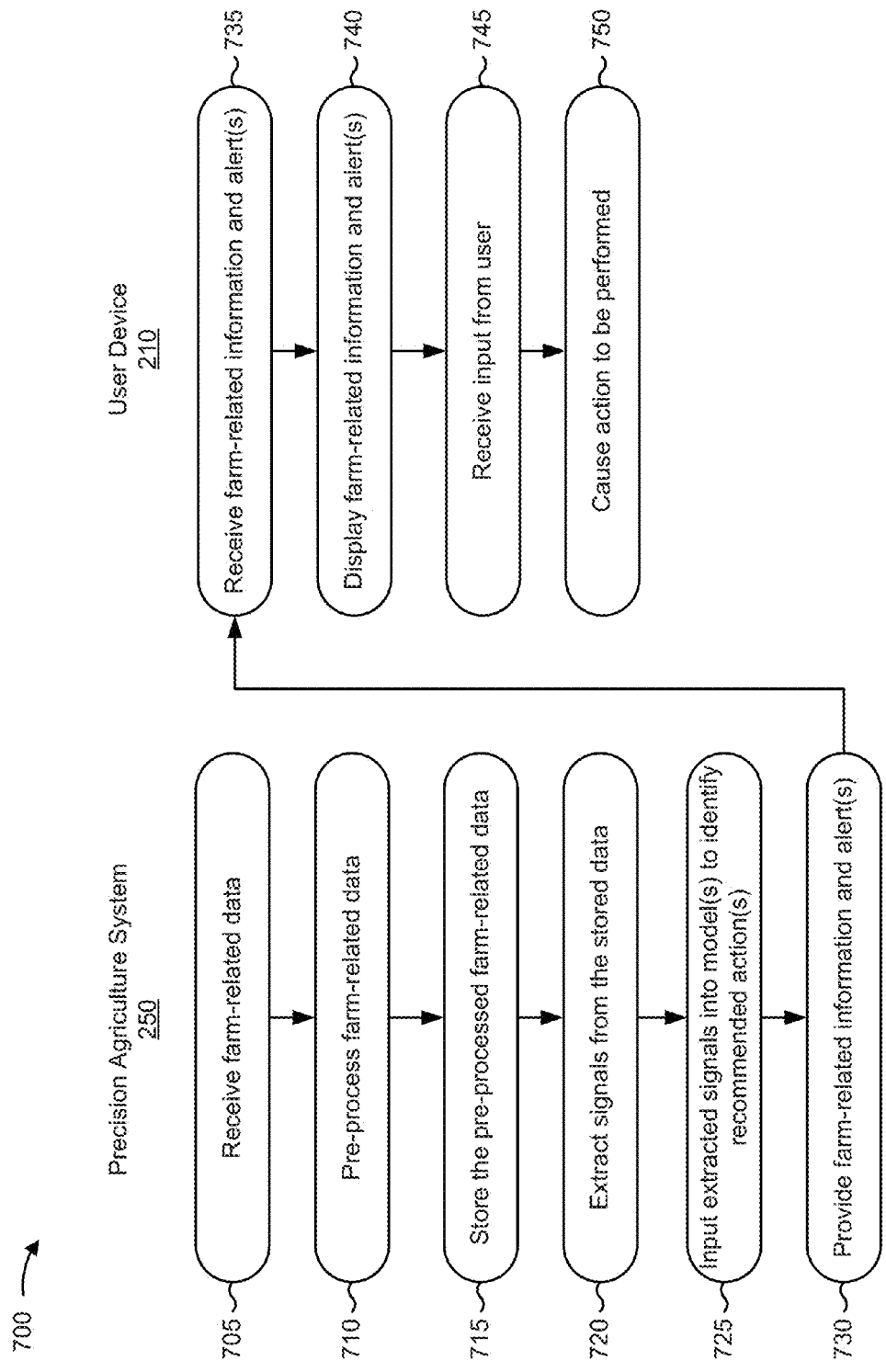
FIG. 7 is a flow chart of an example process for causing a farming-related activity to be performed in connection with a farm.

FIG. 7 is a flow chart of an example process 700 for causing a farming-related activity to be performed in connection with a farm. In some implementations, one or more blocks of FIG. 7 may be performed by precision agriculture system 250 and user device 210. In some implementations, one or more blocks of FIG. 7 may be performed by another device or a group of devices separate from or including precision agriculture system 250 and user device 210.

As shown in FIG. 7, process 700 may include receiving farm-related data (block 705). For example, precision agriculture system 250 may receive farm-related data. The farm-related data may include data from sensor devices 220 located on the farm. The data may include data from a camera (e.g., a visual spectrum imaging camera, an infrared or near infrared imaging camera, etc.), a sap flow sensor, a temperature sensor, a soil temperature sensor, a water sensor, a wind sensor, and/or another type of sensor/device located on or near the farm. The farm-related data may also include data, relevant to the farm, from one or more external information sources 240. The data may include data from a server that provides a Doppler weather forecast, a server that provides imagery or index information from government and/or academic sources, a server that provides market data for specific crops, the USDA "soil type" database, a server that provides historical growth trends for particular crops, and/or another similar type of source. In some implementations, a piece of data may be associated with information identifying a geographic location to which the data is associated and a date and/or time with which the data is associated. For example, if the data is from a soil temperature sensor, the data may be associated with the geographic location of the soil temperature sensor and the date/time at which the sensor reading occurred.

In some implementations, precision agriculture system 250 may receive the farm-related data passively. In some implementations, precision agriculture system 250 may receive the farm-related data based on requesting the farm-related data from a particular source (e.g., from a sensor device 220 and/or from an external information source 240). In addition, in some implementations, precision agriculture system 250 may receive the farm-related data in real time, near real time, or at a particular time period.

As shown in FIG. 7, process 700 may include pre-processing the farm-related data (block 710). For example, precision agriculture system 250 may pre-process the farm-related data to put the farm-related data into a format for use with the models associated with precision agriculture system 250. In some implementations, the pre-processing may include, as described above in connection with block 420 of FIG. 4, filtering the data, normalizing the data, grouping data, etc.

As shown in FIG. 7, process 700 may include storing the pre-processed farm-related data (block 715). For example, precision agriculture system 250 may store the pre-processed farm-related data in a data structure. The data structure may be located within precision agriculture system 250 or external, and possibly remote from, precision agriculture system 250. In some implementations, the data structure may be associated with application database 230.

As shown in FIG. 7, process 700 may include extracting signals from the stored data (block 720). For example, precision agriculture system 250 may extract one or more signals from the data stored in the data structure. The extracted signals may relate to data obtained by a sensor device 220 and/or data obtained from an external information source 240 and may be relevant to farm-related information (e.g., recommendations and/or alerts) to be provided to user device 210, by precision agriculture system 250. For example, for a particular plot of the farm, precision agriculture system 250 may extract, from the stored data, current soil temperature information, current sap flow information, etc.

In some implementations, the particular signals extracted from the stored data may be based on information stored by a user, associated with the farm. For example, as described above in connection with FIG. 6, a user may provide configuration parameters, to precision agriculture system 250, relating to what type of farm-related information and recommendations to provide to user device 210. Thus, precision agriculture system 250 may extract signals from the stored data based on the configuration parameters.

In some implementations, precision agriculture system 250 may extract the signals based on the occurrence of an event. For example, precision agriculture system 250 may extract the signals based on the user, associated with the farm, logging into the PAS application, associated with precision agriculture system 250. In some implementations, precision agriculture system 250 may extract the signals at a predetermined time or in predetermined intervals.

As shown in FIG. 7, process 700 may include inputting the extracted signals into model(s) to identify recommended action(s) (block 725). For example, precision agriculture system 250 may determine recommended actions, relating to the farm, based on inputting the extracted signals into the models. The recommended actions may be based on alerts identified by precision agriculture system 250. The alerts may include an alert relating to a farm device 260 (e.g., that a potential issue exists regarding the farming device), an alert relating to a plot (e.g., that a potential issue exists regarding the plot), a financial alert (e.g., information regarding a time to harvest a crop in the plot, whether to store or sell the crop, etc.), etc. The recommended actions relating to those alerts may include an action to perform in relation to farm device 260 (e.g., to visually inspect the farm device), an action to perform in relation to the plot (e.g., to automatically or visually inspect the plot), an action to perform in relation to the crop (e.g., to harvest the crop, to sell the crop, or the like), etc. The recommended actions may include actions that may be automatically performed (e.g., turning on an irrigation system) or manually performed (e.g., by one or more of the farm's workers). In some implementations, precision agriculture system 250 may provide multiple recommended actions relating to a particular alert and may rank the recommended actions based on one or more factors.

In some implementations, precision agriculture system 250 may determine a financial impact of performing or not performing a recommended action. Thus, precision agriculture system 250 may link a recommended action to a positive or negative financial impact. In some implementations, precision agriculture system 250 may link each recommended action to a financial impact. In those implementations where precision agriculture system 250 provides multiple recommended actions, precision agriculture system 250 may rank the recommended actions based on their financial impacts. Precision agriculture system 250 may determine the financial impact of performing or not performing a particular recommended action, based on static data (e.g., the cost of the land, the cost of a chemical to be used to treat a particular plot, and/or other types static data) and/or variable data (e.g., sensor data, market data relating to a crop with which the particular recommended action is associated, the quantity of a plot that needs to be treated, and/or other types of variable data). For example, assume that precision agriculture system 250 determines, based on sensor data, that an irrigation system associated with a plot may be malfunctioning and that the recommended action is to visually inspect the irrigation system. Precision agriculture system 250 may determine the financial impact not performing the recommended action, based, for example, on the negative effect that not watering the plot will have on the crop in that plot. For example, not watering the plot may cause less yield to be produced by the plot and precision agriculture system 250 may determine the loss in revenue as the financial impact of not performing the recommended action.

As shown in FIG. 7, process 700 may include providing farm-related information and alert(s) (block 730). For example, precision agriculture system 250 may provide farm-related information and alert(s) to user device 210. Precision agriculture system 250 may provide the farm-related information and alert(s) based on the occurrence of an event, such as detecting that the user logged into the PAS application, receiving a request from user device 210, detecting a particular date/time, or the like. The farm-related information may include weather forecast information, sensor information, scheduled activities, commodity prices and trends, analytics and/or reports relating to the farm, product inventory and forecasts, and/or other similar types of information. As set forth above, the alerts may relate to a farm device 260 (e.g., that a potential issue exists regarding the farming device), a plot (e.g., that a potential issue exists regarding the plot, information regarding a time to harvest a crop in the plot), a crop (e.g., whether to store or sell the crop), etc. Each alert may be associated with one or more recommended courses of action.

As shown in FIG. 7, process 700 may include receiving the farm-related information and alert(s) (block 735) and displaying the farm-related information and alert(s) (block 740). For example, user device 210 may receive the farm-related information and alert(s) from precision agriculture system 250 via a network, such as network 270. User device 210 may cause the farm-related information and/or alert(s) to be displayed. In some implementations, user device 210 may display the farm-related information and/or alert(s) based on the configuration parameters set in relation to block 610 of FIG. 6.

As shown in FIG. 7, process 700 may include receiving an input from the user (block 745) and causing an action to be performed based on the input (block 750). For example, user device 210 may receive an input from the user of user device 210. In some implementations, the user may select an alert displayed via a user interface of user device 210. Based on the selection, user device 210 may cause a user interface to be displayed with one or more recommended courses of action relating to the alert. In some implementations, each recommended course of action may be associated with a financial impact of performing or not performing the recommended course of action. In some implementations, the user interface may permit the user to automatically perform an act based on selection of one of the recommended courses of action. The act may be to automatically schedule a worker to perform a manual operation, to automatically schedule a company to visit the farm to perform an action (e.g., to perform maintenance on a farm device 260), to automatically turn on (or off) a farm device 260 (e.g., an irrigation system), to automatically cause a farm device 260 to perform an action (e.g., causing a UAV to visually inspect a plot), or the like.

As set forth above, user device 210 may provide the results of performing a recommended action to precision agriculture system 250. Precision agriculture system 250 may update one or more models based on the results.

Although FIG. 7 shows example blocks of process 700, in some implementations, process 700 may include additional blocks, fewer blocks, different blocks, or differently arranged blocks than those depicted in FIG. 7. Additionally, or alternatively, two or more of the blocks of process 700 may be performed in parallel.

Figure 8:
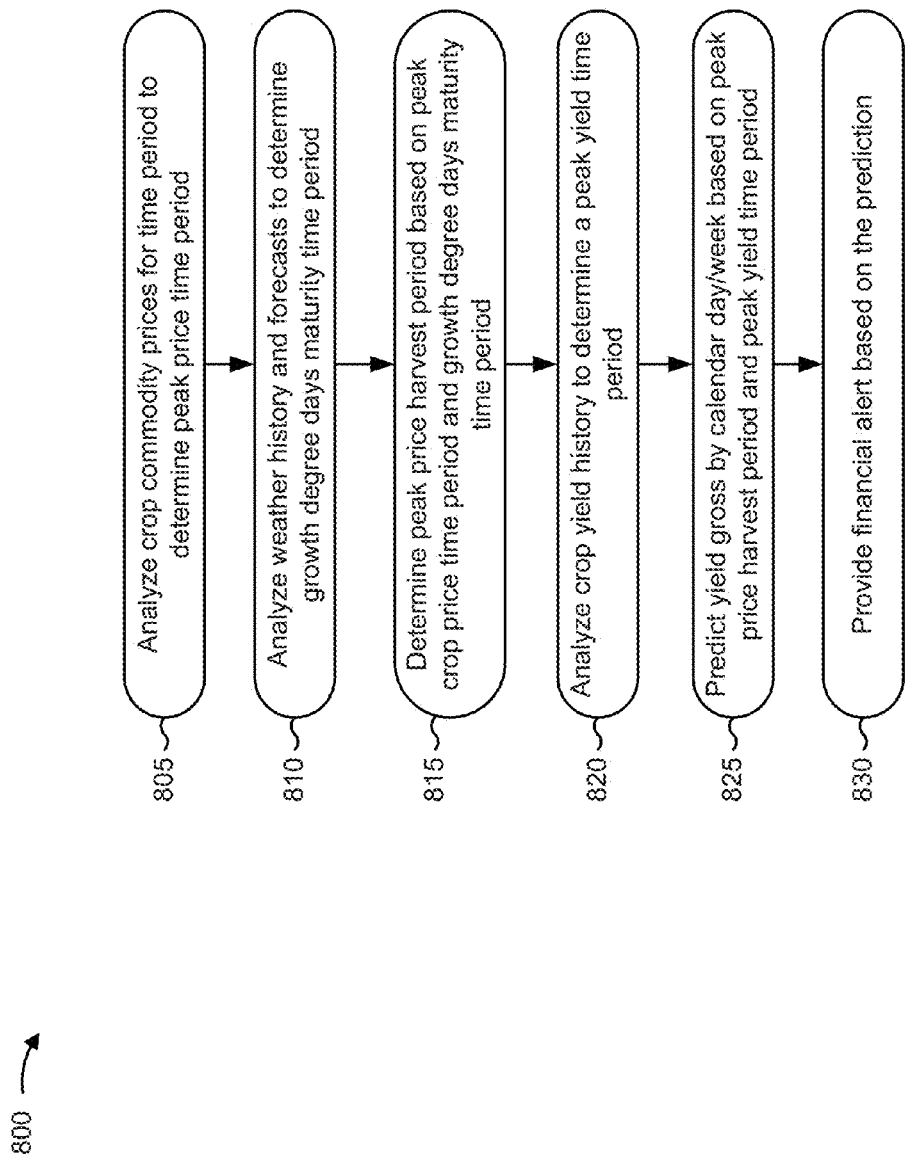
FIG. 8 is a flow chart of an example process for generating a financial alert.

FIG. 8 is a flow chart of an example process 800 for generating a financial alert. Process 800 may relate to block 725 of FIG. 7. In some implementations, one or more blocks of FIG. 8 may be performed by precision agriculture system 250. In some implementations, one or more blocks of FIG. 8 may be performed by another device or a group of devices separate from or including precision agriculture system 250.

As shown in FIG. 8, process 800 may include analyzing crop commodity prices for a time period to determine a peak price time period (block 805). For example, precision agriculture system 250 may analyze crop commodity prices, for a particular crop, for a particular time period (e.g., for the past 48 months). Based on this analysis, precision agriculture system 250 may calculate the standard deviation, in calendar days, of the peak price per bushel of the crop to obtain a result, called the Peak Standard Deviation Days. Precision agriculture system 250 may also calculate the average day of occurrence of the peak price for the crop to obtain a result, called the Average Occurrence Day. Precision agriculture system 250 may then use the Peak Standard Deviation Days plus and minus the Average Occurrence Day to identify a result, called the Peak Price Time Period, which is a set of calendar days during which typical peak pricing, for the crop, occurs during the year. Precision agriculture system 250 may calculate the average peak price of the crop over the particular time period to obtain a result, called the Average Peak Price. Precision agriculture system 250 may also calculate the standard deviation of the price over the Peak Price Time Period for each time cycle (e.g., for each 12 month time cycle), during the particular time period, and average the standard deviations of the price to obtain a result, called the Average Standard Deviation Peak Price.

As shown in FIG. 8, process 800 may include analyzing weather history and forecasts to determine a growth degree days maturity time period (block 810). For example, precision agriculture system 250 may analyze weather history and forecasts. Based on this analysis, precision agriculture system 250 may calculate the current growth degree days, called the Current GDD, for the crop based on weather history from an external information source 240, such as local agricultural weather station sensors. Precision agriculture system 250 may also calculate the growth degree days required for the maturity of the crop, called the GDD Required. Precision agriculture system 250 may calculate GDD Required based on the type of the crop and based on information from an external information source 240, such as information from a university or USDA guidelines.

Precision agriculture system 250 may calculate a target maturity date, called the GDD Target Maturity Date, based on weather forecasts (e.g., based on determining a particular date, Dn, from the following equation: GDD Required−D1−D2−D3− . . . −Dn=0, where D1 is the forecasted growth degree days for the following day, D2 is the forecasted growth degree days for the next day, until the difference is 0). Precision agriculture system 250 may then calculate GDD Target Maturity Date as follows:

$$\text{GDD Target Maturity Date} = \text{Current Date} + D_n.$$

In some implementations, the above calculations may be based on the commonly accepted GDD=((Tmax+Tmin)/2)−Tbase equation method for calculating growth degree days. Other methods may alternatively be used.

Precision agriculture system 250 may calculate the standard deviation of the growth degree days maturity dates over the particular time period to obtain a result, called the GDD Maturity Standard Deviation. Precision agriculture system 250 may calculate a growth degree days maturity time period, called the GDD Time Period, using the GDD Maturity Stand Deviation plus and minus the GDD Maturity Date. Finally, precision agriculture system 250 may analyze warnings about inclement weather and the effect that the inclement weather may have on the GDD Time Period calculation and revise the GDD Time Period calculation based on this analysis.

As shown in FIG. 8, process 800 may include determining a peak price harvest period based on peak crop price time period and growth degree days maturity time period (block 815). For example, precision agriculture system 250 may determine a peak price harvest period, called the Peak Price Harvest Period, based on the Peak Price Time Period and the GDD Time Period. In some implementations, precision agriculture system 250 may determine Peak Price Harvest Period as a time period where the Peak Price Time Period and the GDD Time Period overlap on the calendar.

As shown in FIG. 8, process 800 may include analyzing crop yield history to determine a maximum yield time period (block 820). For example, precision agriculture system 250 may analyze the crop yield history for the particular time period. Based on this analysis, precision agriculture system

250 may calculate a standard deviation of the crop yield, called the Yield Standard Deviation, for the same crop, in the same plot, over the particular time period. Precision agriculture system 250 may also predict a crop yield, called the Current Predicted Yield, based on growth trend modeling using for example, aerial surveys, LiDAR volume measurements, and trending analysis techniques. Precision agriculture system 250 may then calculate a weighted predicted yield for the crop (Weighted Predicted Yield), as follows:

Weighted Predicted Yield=(History Yield Average+ Current Predicted Yield)/2 where History Yield Average is the average yield for the crop, in the plot, over the particular time period. Precision agriculture system 250 may calculate the peak yield time period, called the Peak Yield Time Period, based on Yield Standard Deviation plus and minus Weighted Predicted Yield.

As shown in FIG. 8, process 800 may include predicting a yield gross by calendar day/week based on the peak price harvest period and the peak yield time period (block 825). For example, precision agriculture system 250 may predict a yield gross for the crop, by calendar day/week, based on Peak Price Harvest Period and Peak Yield Time Period. In some implementations, precision agriculture system 250 may determine the predicted yield gross based on the crop prices, during Peak Price Time Period, and the crop yields, during Peak Yield Time Period.

As shown in FIG. 8, process 800 may include providing a financial alert based on the prediction (block 830). For example, precision agriculture system 250 may provide a financial alert, to user device 210, based on the predicted yield gross. Precision agriculture system 250 may also use the above techniques to determine the financial impact of performing or not performing a recommended course of action.

Although FIG. 8 shows example blocks of process 800, in some implementations, process 800 may include additional blocks, fewer blocks, different blocks, or differently arranged blocks than those depicted in FIG. 8. Additionally, or alternatively, two or more of the blocks of process 800 may be performed in parallel.

Figure 9A:
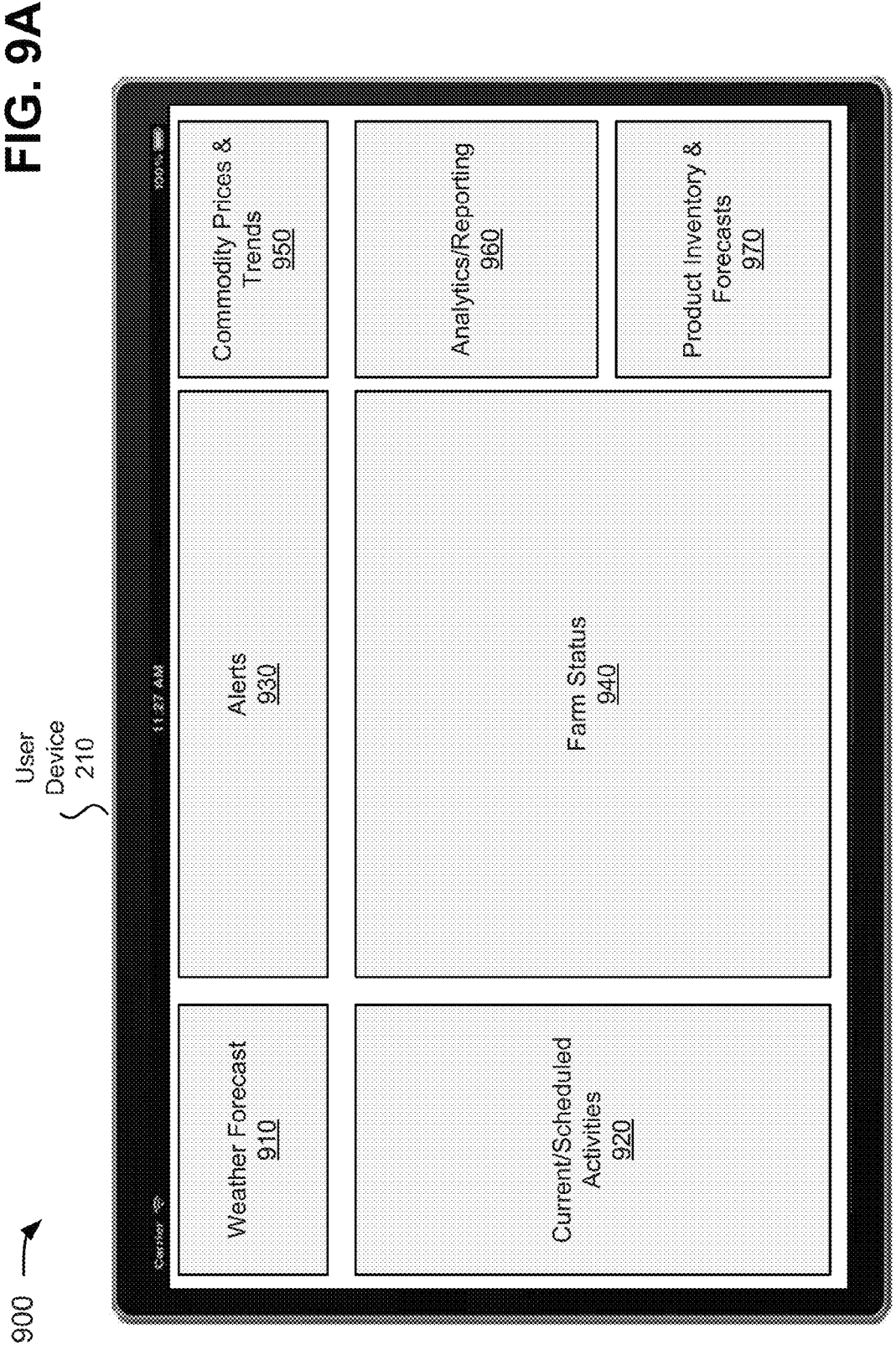
FIG. 9A is an example configuration of a user interface that may be provided to a user device.

FIG. 9A is an example configuration of a user interface 900, associated with the PAS application, that may be provided to a user device 210. As shown, user interface 900 may include a group of sections, including a weather forecast area 910, a current/scheduled activities section 920, an alerts section 930, a farm status section 940, a commodity prices & trends section 950, an analytics/reporting section 960, and a product inventory & forecasts section 970.

Weather forecast section 910 may include a section, of user interface 900, that provides weather information. For example, weather forecast section 910 may provide weather feeds by plot/area of the farm. In some implementations, weather forecast section 910 may include a map view that depicts localized weather sensors on a map of the farm. Current/scheduled activities section 920 may include a section, of user interface 900, that provides information relating to activities that are either occurring at the farm or are scheduled to occur at the farm. For example, current/ scheduled activities section 920 may provide information that allows a user to manage the farm by viewing details regarding current/scheduled activities, assigning activities to a farm device 260, a worker, and/or an outside vendor, etc.

Alerts section 930 may include a section, of user interface 900, that provides information relating to alerts associated with the farm. For example, alerts section 930 may provide an alert relating to a farm device 260 (e.g., that a potential issue exists regarding the farming device), an alert relating a plot (e.g., that a potential issue exists regarding the plot), a financial alert (e.g., information regarding a time to harvest a crop in the plot, whether to store or sell the crop, etc.), and/or other types of alerts. Alert section 930 may further provide a map that visually identifies a location of an alert. Alerts section 930 may also provide recommended courses of action relating to alerts.

Farm status section 940 may include a section, of user interface 900, that provides information relating to the status of sensor devices 220 and/or farm devices 260 associated with the farm. For example, farm status section 930 may provide a map that visually depicts the location and status of sensor devices 220, sensor readings, farm devices 260, operational status of farm devices 260, etc. In some implementations, farm status section 940 may display the status of a particular plot of the farm in a heat map fashion, where, for example, green areas indicate that no issues have been identified, yellow areas indicate that potential issues exist, and red areas indicate that issues have been identified.

Commodity prices & trends section 950 may include a section, of user interface 900, that provides information relating to crop pricing and predictions. For example, commodity prices & trends section 950 may provide commodity pricing, yield forecasting by crop and/or plot, and/or other similar types of information. Analytics/reporting section 960 may include a section, of user interface 900, that provides reports relating to the farm. For example, analytics/reporting section 960 may provide reports based on current information, reports based on historical information, and/or reports relating to forecasted information. In some implementations, analytics/reporting section 960 may provide visual information that allows the user to view information over time (e.g., from a previous time period, to a current time period, to a predicted future time period). For example, analytics/reporting section 960 may provide the progression of a plot using a progression of images and/or video. Product inventory & forecasts section 970 may include a section, of user interface 900, that provides information relating to crop inventory. For example, product inventory & forecasts section 970 may provide information that allows a user to manage inventory (e.g., by adding inventory, selling inventory, storing inventory, harvesting inventory, etc.).

Although FIG. 9A shows an example configuration of user interface 900, in some implementations, user interface 900 may include additional sections/elements, different sections/elements, fewer sections/elements, or differently arranged sections/elements than those depicted in FIG. 9A.

Figure 9B:
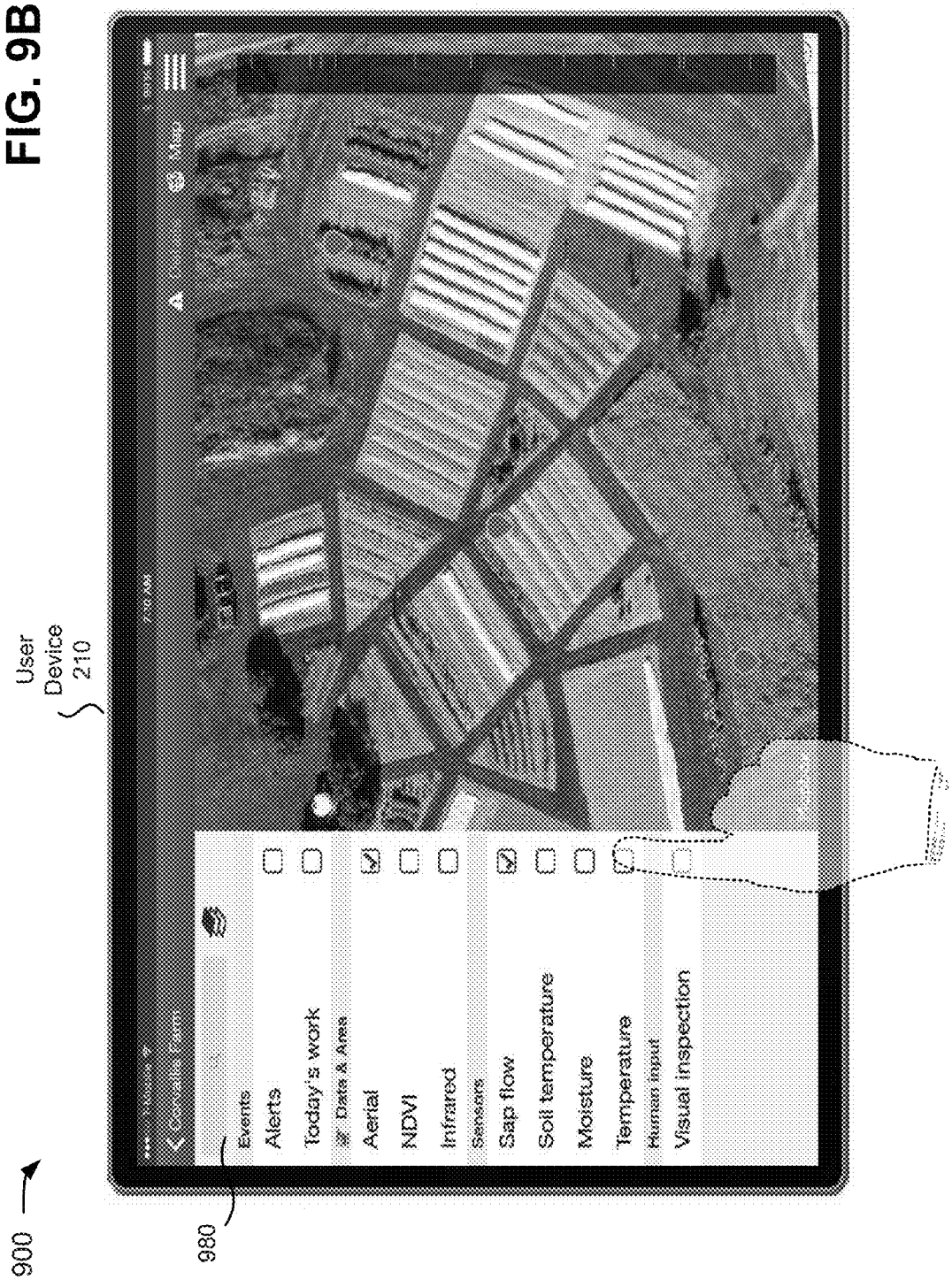
FIGS. 9B-9E are examples of the display of different image types and sensors via a user interface.

FIGS. 9B-9E are examples of the display of different image types and sensors via user interface 900. With reference to FIG. 9B, assume that a user, of user device 210, has requested that aerial imagery of the user's farm be shown, along with the location of sap flow sensors. In response, precision agriculture system 250 may provide user interface 900, as shown in FIG. 9B. As shown, user interface 900 includes a section 980 that allows the user to select information to be displayed in user interface 900. For example, section 980 includes an events section (that allows the user to identify the location of events and ongoing work), a data & area section (that allows the user to identify the type of visual map to provide), a sensors section (that allows the user to identify the type of sensor(s) to display), and a human input section (that allows the user to identify the location of areas that have been visually inspected). Assume that the user also wishes to see the location of temperature sensors.

As a result, the user may select the temperature sensor from section 980 of user interface 900.

Figure 9C:
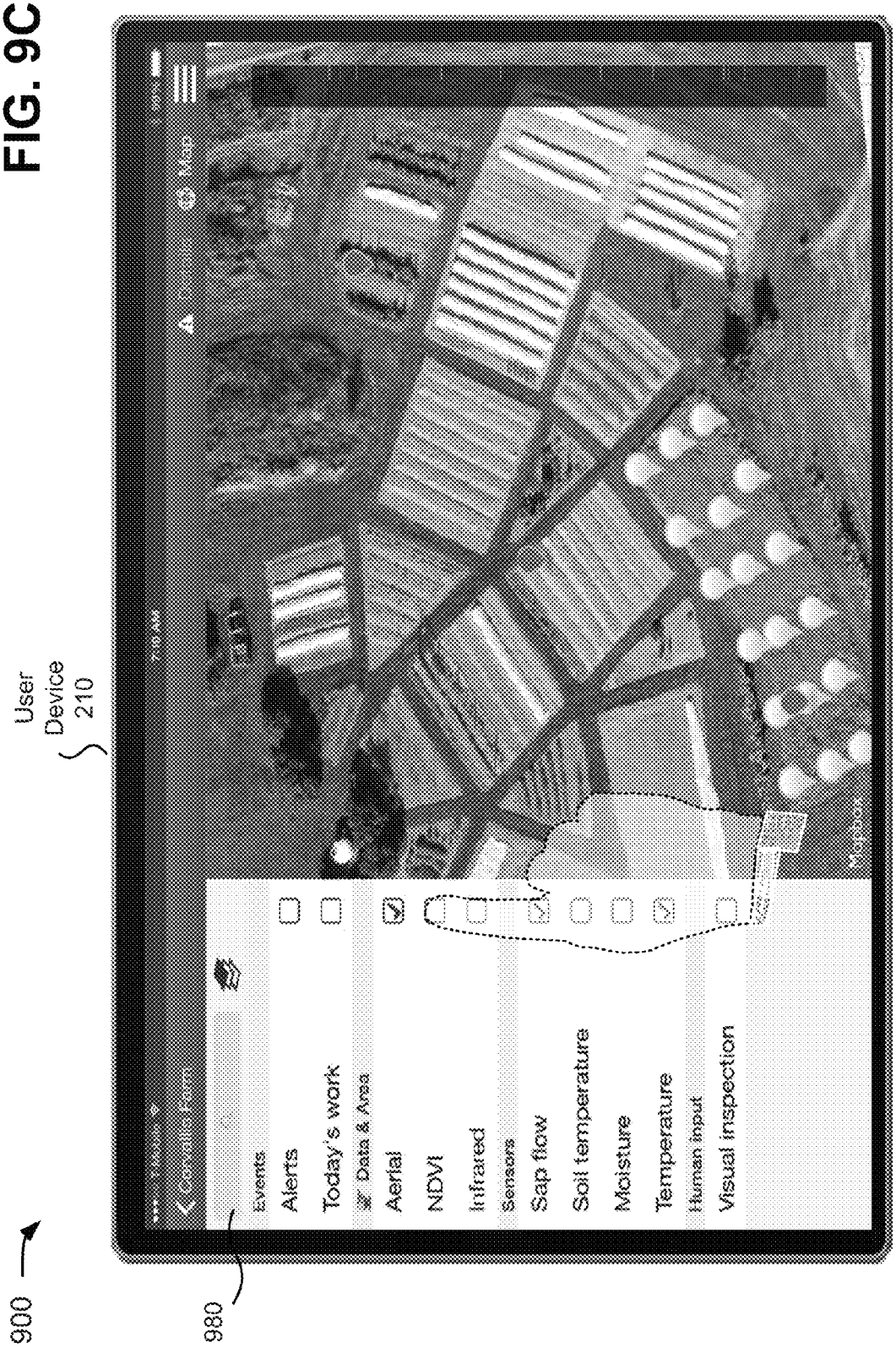

With reference to FIG. 9C, user interface 900 now displays the location of the sap flow sensors and the temperature sensors. These sensors are displayed in different colors to help distinguish the different types in user interface 900. Assume that, at some later point in time, the user is interested in now viewing the map using NDVI imagery. Thus, the user may select NDVI from section 980 of user interface 900.

Figure 9D:
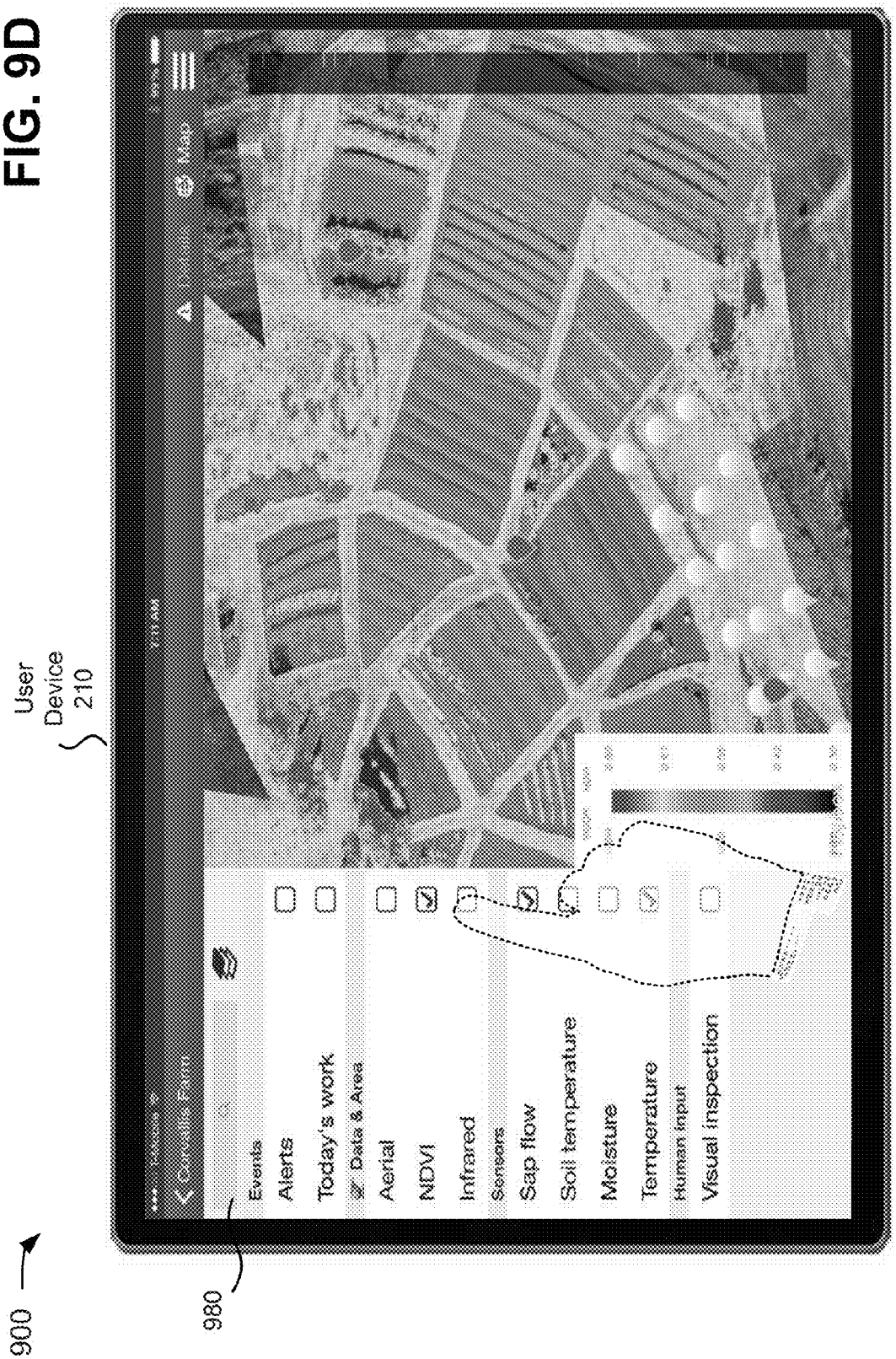
Figure 9E:
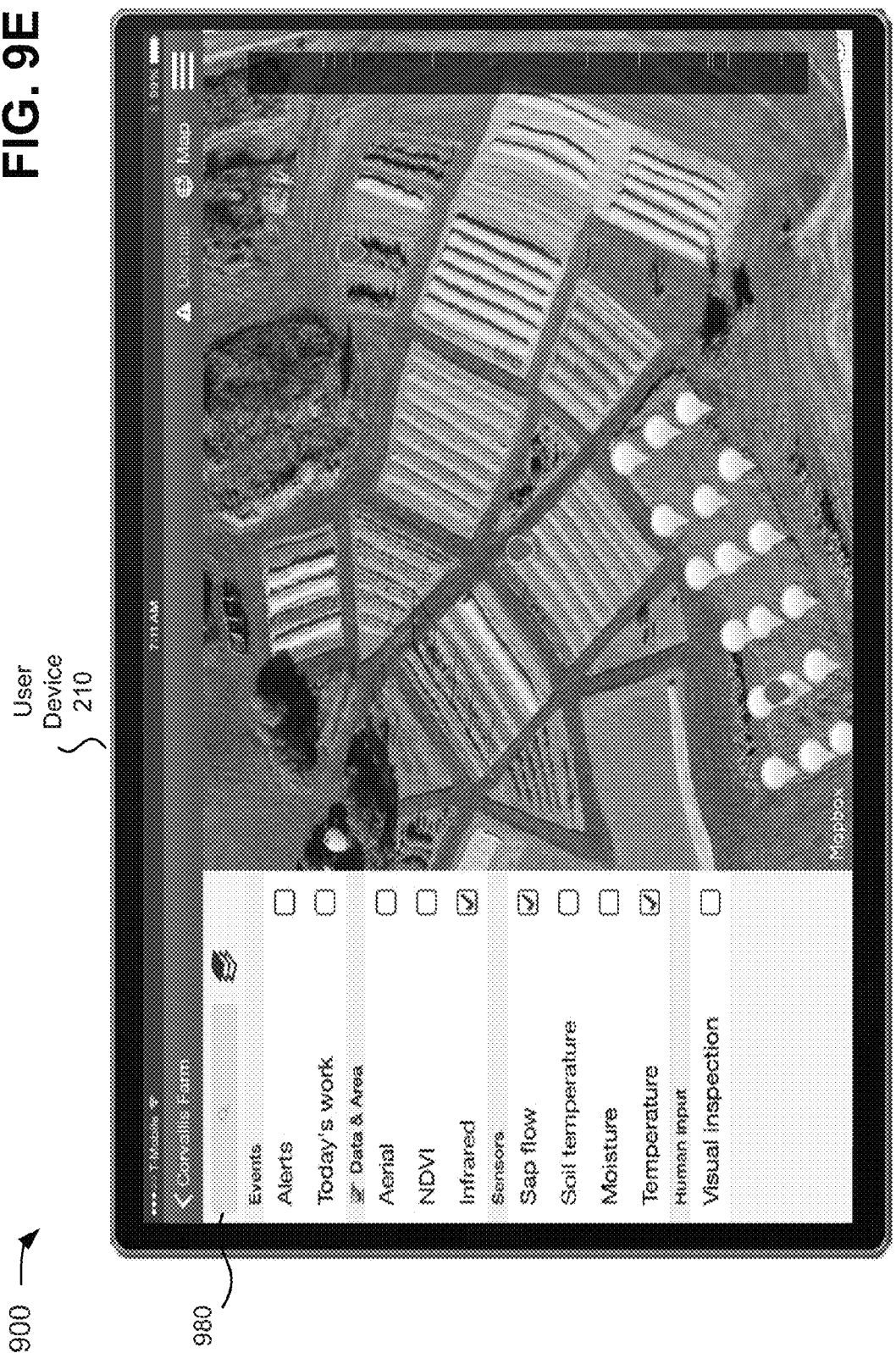

With reference to FIG. 9D, user interface 900 now displays the location of the sap flow sensors and the temperature sensors, and displays the map using aerial NDVI imagery. Finally, assume that, at some later point in time, the user is interested in now viewing the map using the infrared imagery. Thus, the user may select infrared from section 980 of user interface 900. With reference to FIG. 9E, user interface 900 now displays the location of the sap flow sensors and the temperature sensors, and displays the map using aerial infrared imagery instead of aerial NDVI imagery.

As indicated above, FIGS. 9B-9E are provided merely as an example. Other examples and imagery types are possible and may differ from what was described with regard to FIGS. 9A-9E.

Figure 10A:
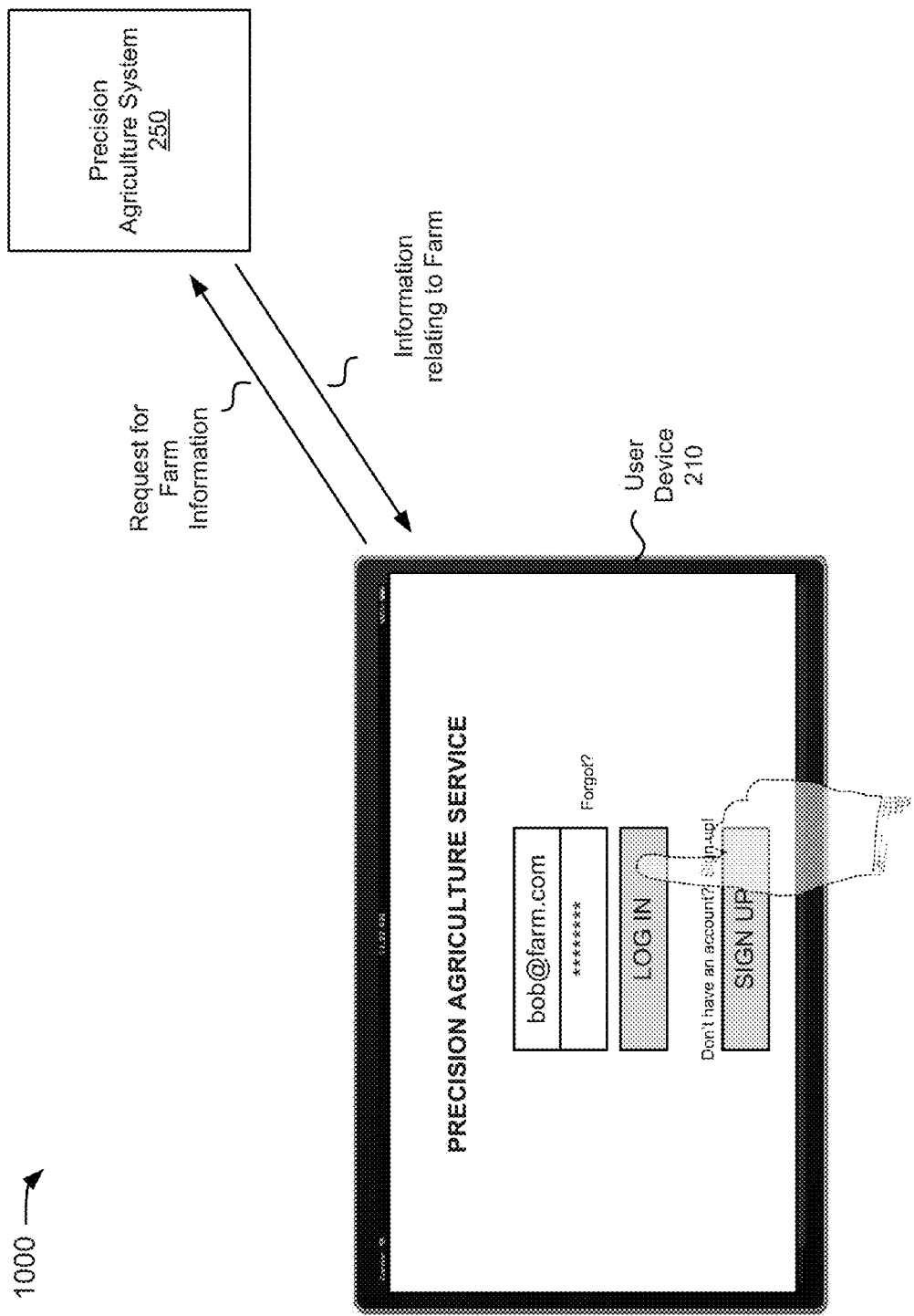

FIGS. 10A-10H are an example 1000 of the process described above with respect to FIG. 7. Example 1000 relates to providing financial alerts. With reference to FIG. 10A, assume a user, named Bob Smith, is a farmer who manages a number of farms. Assume further that Bob Smith has installed the PAS application and has registered with precision agriculture system 250, as described above in relation to FIG. 6, to obtain the precision agriculture service. As shown in FIG. 10A, Bob may log into the precision agriculture service by entering a user name and password. Based on selecting the log in button on user device 210, user device 210 may send a request for farm information to precision agriculture system 250. The request may include Bob's log in information. Precision agriculture system 250 may validate Bob's log in information and, once validated, send information relating to the farm(s) with which Bob is associated.

Figure 10C:

With reference to FIG. 10B, user device 210 displays a welcome screen and a list of farms with which Bob is associated. As shown, assume that Bob selects the Corvallis farm. With reference to FIG. 10C, user device 210 may display a user interface that includes information relating to the Corvallis farm. As shown, the user interface includes information identifying a location of the Corvallis farm (shown as being in Middleburg), current temperature information for Middleburg, and market information for the crops grown on the Corvallis farm. In addition, the user interface includes an alerts section 1005, a map section 1010 showing pins related to sensors on the farm, and a tasks section 1015 showing a list of active tasks. Assume that Bob wishes to view financial alerts. As a result, Bob may select the financial alert in alerts section 1005.

Figure 10D:
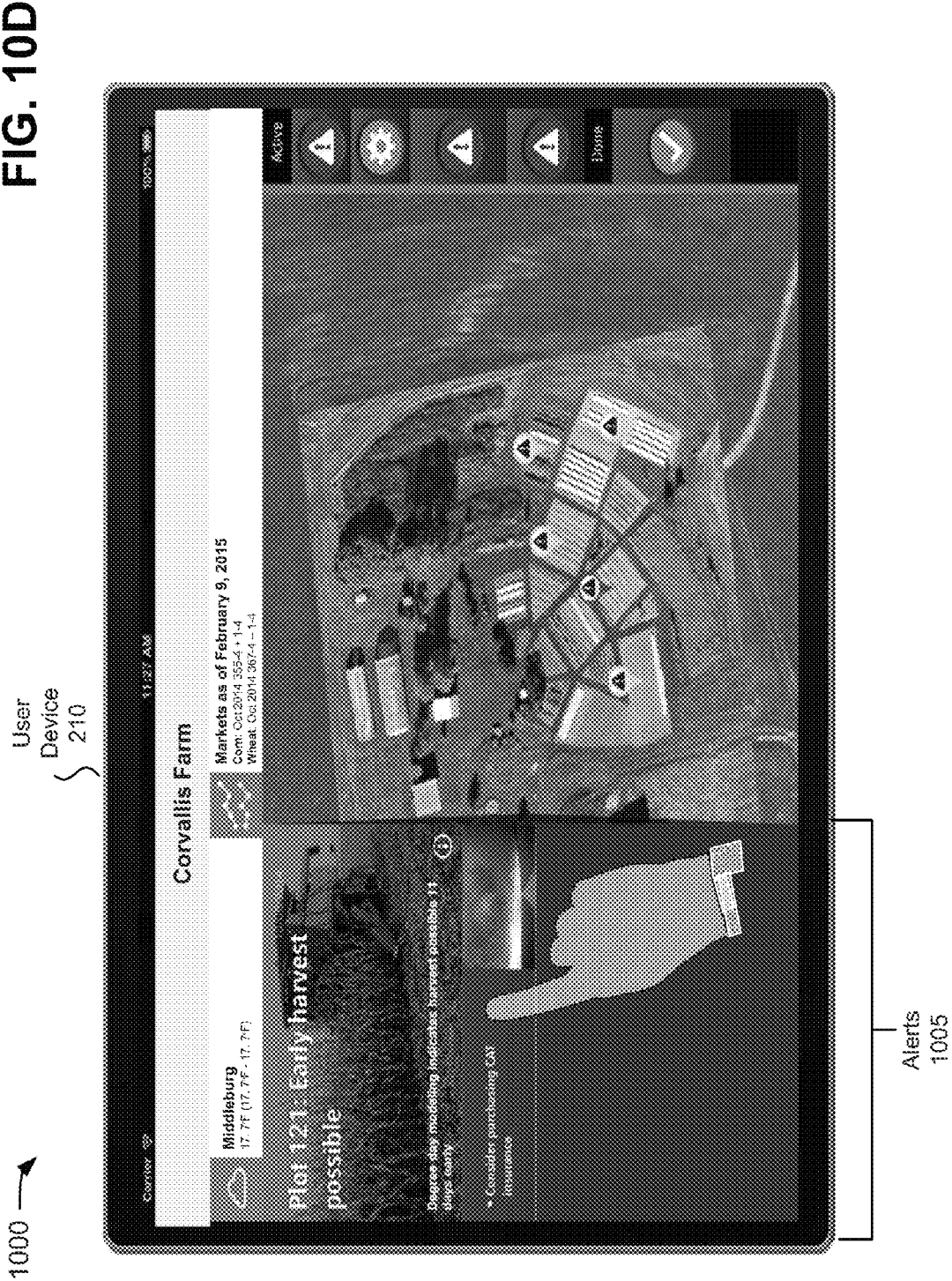
Figure 10E:
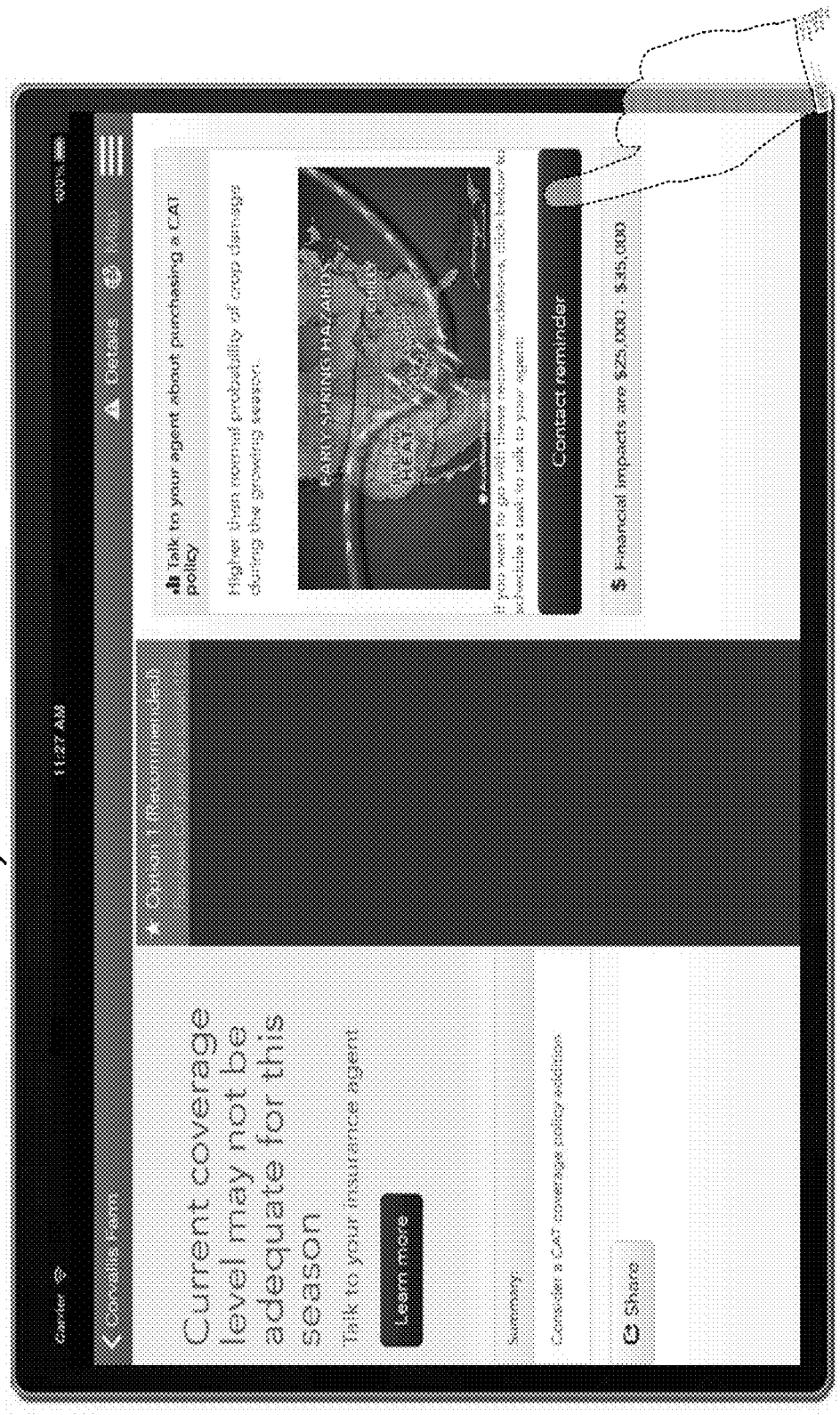

With reference to FIG. 10D, user device 210 displays the current financial alerts in alerts section 1005. As shown, the financial alerts include a first alert relating to a possible early harvest of plot 121 and a second alert relating to the purchase of catastrophic (CAT) insurance. Assume that Bob selects the second alert. With reference to FIG. 10E, user device 210 displays detailed information relating to the second alert. As shown, user device 210 displays a recommendation to increase the CAT insurance for the Corvallis farm. User device 210 also displays the financial impact of not increasing the insurance coverage. Finally, user device 210 provides a graphical element (shown as a Contact reminder button) that allows the user to schedule a task to talk to the insurance agent about the increase in coverage. Assume that Bob selects the button. As a result, user device 210 sends a notice to precision agriculture system 250, which, in turn, schedules a task for Bob.

Figure 10F:
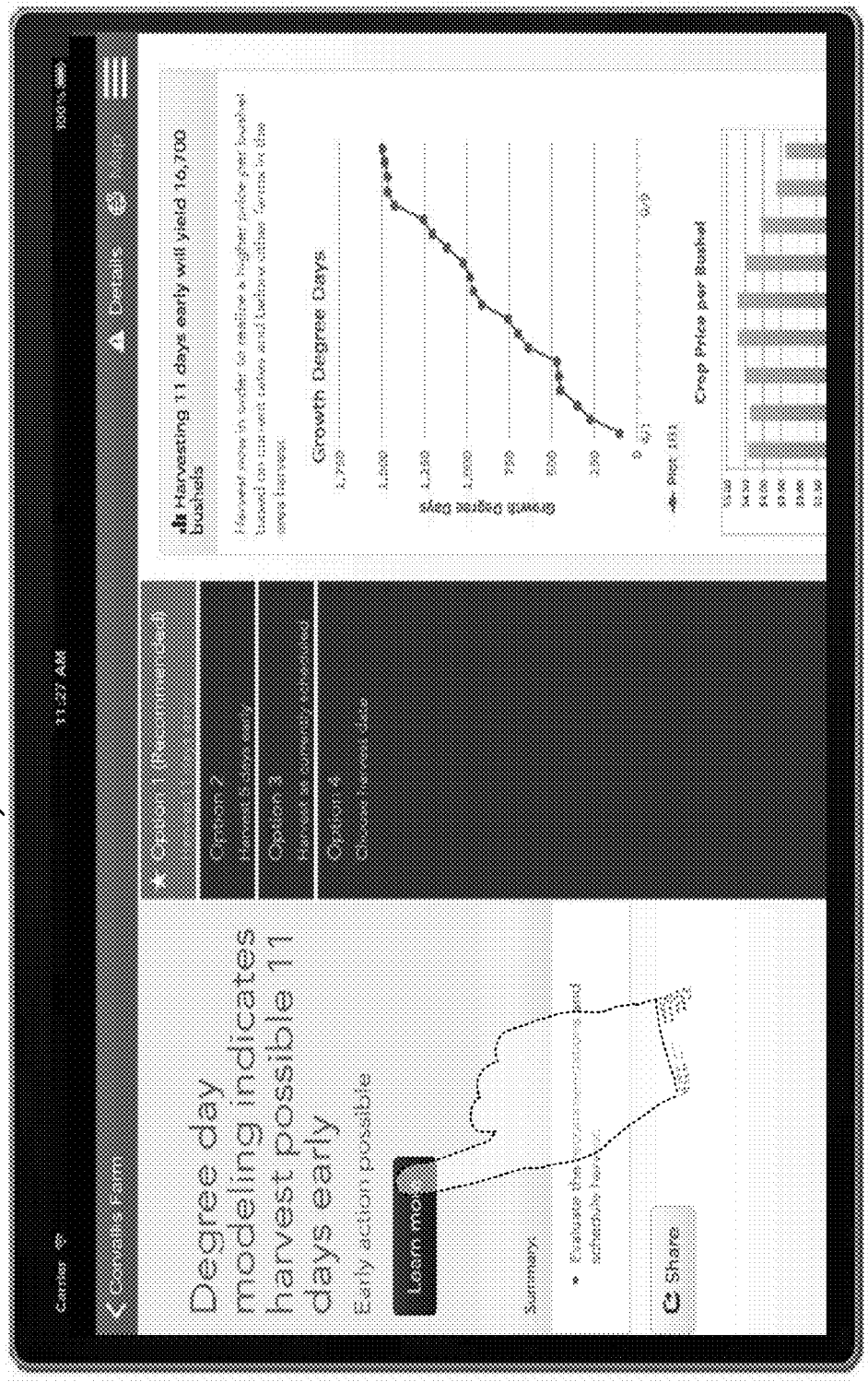

Returning to FIG. 10D, assume that Bob now selects the first alert. With reference to FIG. 10F, user device 210 displays a recommendation regarding performing an early harvest of the crop in plot 121. As shown, user device 210 displays four recommendations relating to the early harvest. The first recommendation relates to harvesting the plot 11 days earlier than currently scheduled. The second recommendation relates to harvesting the plot 5 days early. The third recommendation relates to harvesting the plot as currently scheduled. The fourth recommendation allows Bob to schedule when he would like to harvest the plot. User device 210 provides details relating to the first recommendation. As shown, by harvesting plot 121 eleven days early, plot 121 is predicted to yield 16,700 bushels and is predicted to result in a higher price per bushel. Assume, as shown, Bob wishes to obtain additional information relating to the first recommendation and, as a result, selects the Learn more button.

Figure 10G:
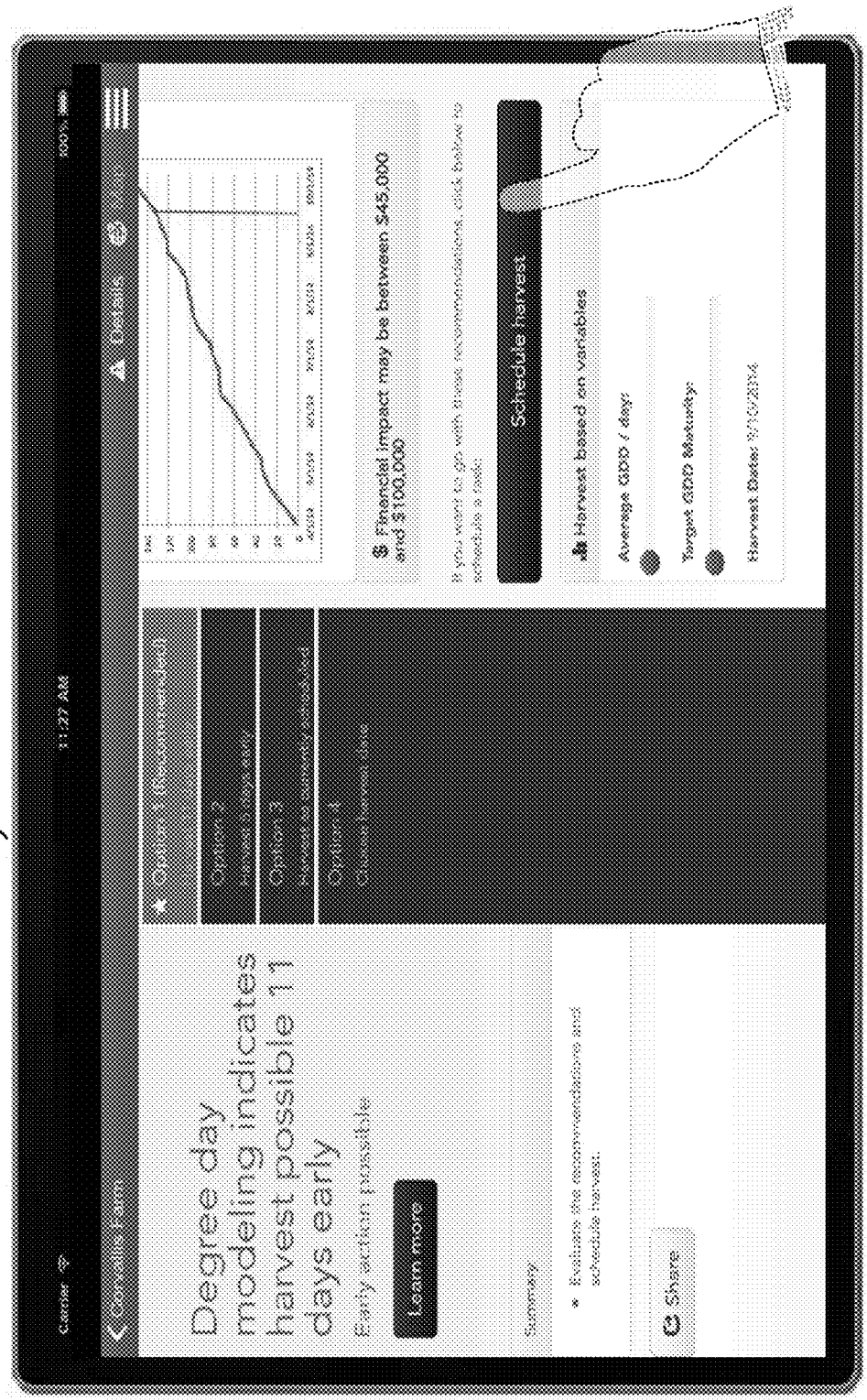

With reference to FIG. 10G, user device 210 provides additional details regarding the first recommendation. As shown, user device 210 indicates that, by harvesting 11 days early, the financial impact may be an increase in revenue between $45,000 and $100,000. User device 210 also provides a button (Schedule harvest) that allows Bob to schedule the harvest of plot 121 eleven days early. Assume Bob selects the button.

With reference to FIG. 10H, user device 210 sends a harvest work order to precision agriculture system 250. The harvest work order identifies plot 121 and that plot 121 is to be harvested on a particular date, which is 11 days earlier than the currently scheduled date. Based on receiving the harvest work order, precision agriculture system 250 may identify a harvest worker (or harvest manager) associated with plot 121 and send the harvest work order to a user device of the harvest worker (or harvest manager). Assume the work order indicates that 500 bushels should be harvested from plot 121. As a result, the harvest worker may harvest 500 bushels of the crop in plot 121. Once the harvest is complete, the harvest worker may cause the user device to send a notification of the completion of the harvest work order to precision agriculture system 250. Precision agriculture system 250 may update one or more models based on the notification.

In addition, precision agriculture system 250 may identify a sales worker (or sales manager) associated with the sale of the crop and send a sale work order to a user device of the sales worker (or sales manager). Assume the sale order indicates that the 500 bushels should be sold to a regional purchaser. The sales worker (or sales manager) may cause the 500 bushels of the crop to be loaded on a truck and delivered to the regional purchaser. The sales worker (or sales manager) may cause the user device to send a notification of the completion of the sale work order to precision agriculture system 250 and precision agriculture system 250 may update one or more models based on the notification.

As indicated above, FIGS. 10A-10H are provided merely as an example. Other examples are possible and may differ from what was described with regard to FIGS. 10A-10H.

Figure 11A:
FIGS. 11A-11D are another example of the process described above with respect to FIG. 7.

FIGS. 11A-1D are another example 1100 of the process described above with respect to FIG. 7. With reference to FIG. 11A, assume, once again, that a user, named Bob Smith, has logged into the PAS application to obtain the precision agriculture service from precision agriculture system 250. In example 1100, assume that user device 210 provides an alert, in alert section 1105, relating to equipment maintenance. Assume further that Bob selects the alert, as shown in FIG. 11A.

Figure 11B:

With reference to FIG. 11B, user device 210 provides a map, in map section 1110, that identifies the location of the equipment, on the farm, via a pin. Assume Bob wishes to obtain further information regarding the alert and, as a result, selects the pin.

Figure 11C:
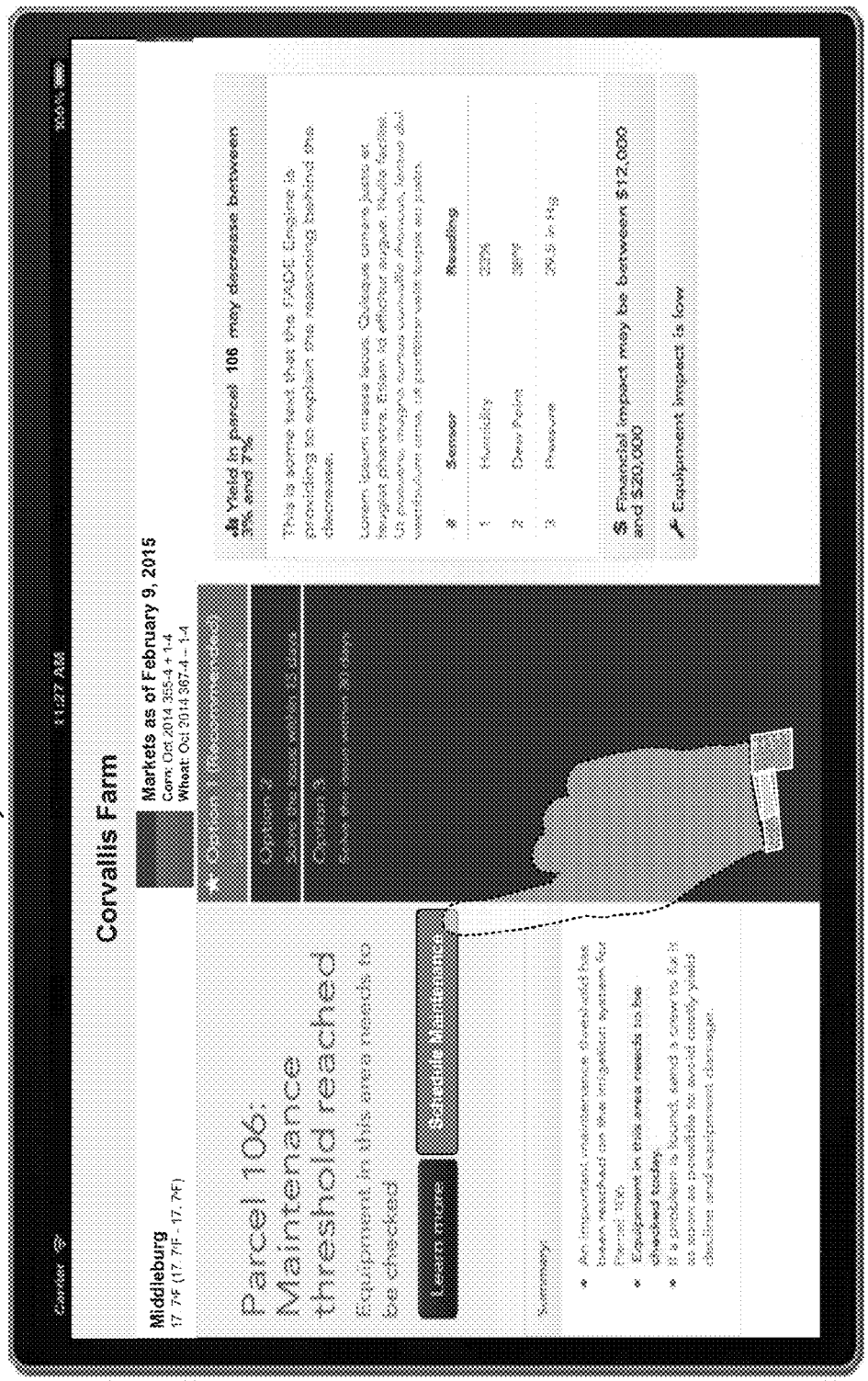

With reference to FIG. 11C, user device 210 displays detailed information relating to the alert. As shown, user device 210 displays three recommendations relating to the equipment maintenance alert. The first recommendation relates to performing the equipment maintenance within the next 8 days. The second recommendation relates to performing the equipment maintenance within the next 15 days. The third recommendation relates to performing the equipment maintenance within the next 30 days. User device 210 provides details relating to the first recommendation. As shown, by not performing the equipment maintenance in the next 8 days, there is a chance that the yield from plot 106, with which the equipment is associated, may decrease by between 3% and 7%. User device 210 also displays the financial impact of not performing the equipment maintenance within the next 8 days. User device 210 further provides a button (Schedule maintenance) that allows Bob to schedule the equipment maintenance. Assume Bob selects the button.

Figure 11D:
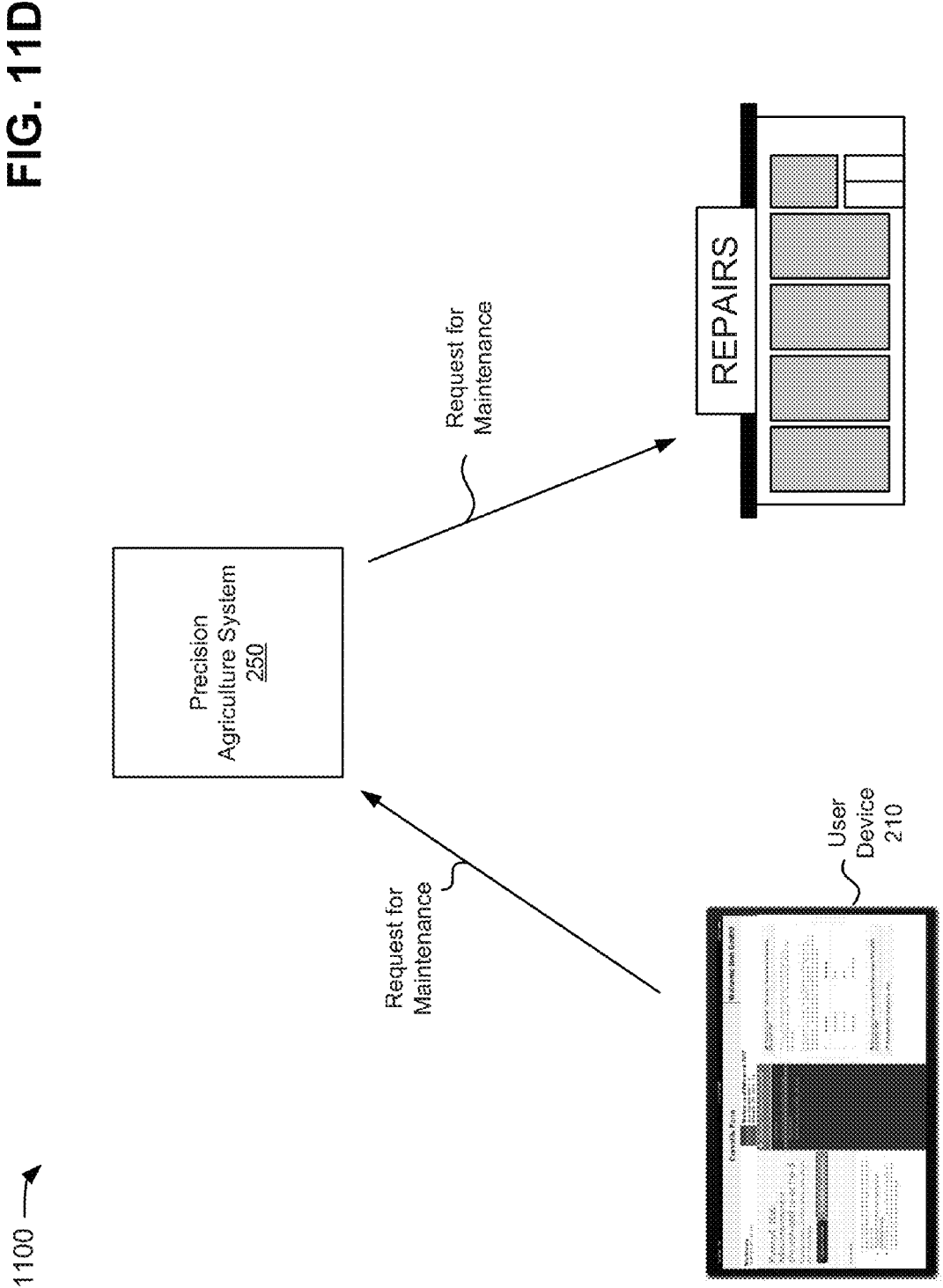

With reference to FIG. 11D, user device 210 sends a request for equipment maintenance to precision agriculture system 250. The maintenance request may include information identifying Bob, the equipment, and a range of dates for which the maintenance work is being requested to be performed. Based on receiving the maintenance request, precision agriculture system 250 may identify a repair shop, associated with the Corvallis farm, and send a maintenance request to the shop. Once the maintenance work is complete, the repair shop or user device 210 may send a notification of the completion of the maintenance work to precision agriculture system 250. Precision agriculture system 250 may update an entry, in one or more models, relating to the equipment based on the received notification.

As indicated above, FIGS. 11A-11D are provided merely as an example. Other examples are possible and may differ from what was described with regard to FIGS. 11A-11D.

Figure 12B:
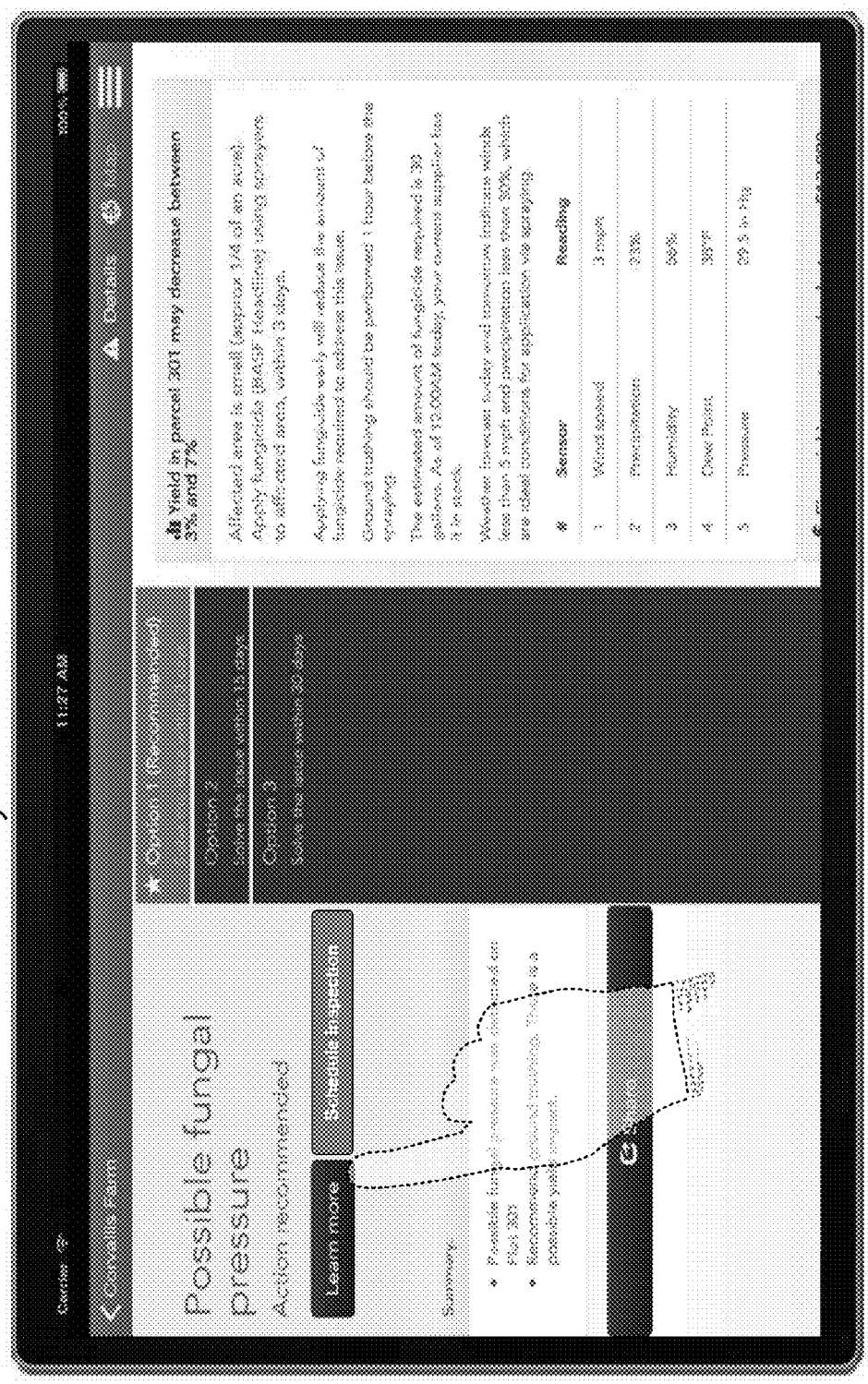

FIGS. 12A-12L are yet another example 1200 of the process described above with respect to FIG. 7. With reference to FIG. 12A, assume, once again, that a user, named Bob Smith, has logged into the PAS application to obtain the precision agriculture service from precision agriculture system 250. In example 1200, assume that user device 210 provides an alert, in alert section 1205, relating to a possible fungal pressure issue at plot 301. Assume further that Bob selects the alert, as shown in FIG. 12A.

With reference to FIG. 12B, user device 210 displays detailed information relating to the alert. As shown, user device 210 displays three recommendations relating to the fungal pressure alert. The first recommendation relates to performing a visual inspection of plot 301 within the next 3 days. The second recommendation relates to performing the visual inspection within the next 15 days. The third recommendation relates to performing the visual inspection within the next 30 days. User device 210 provides details relating to the first recommendation. As shown, by not performing the visual inspection in the next 3 days, there is a chance that the yield from plot 301 may decrease by between 3% and 7%. User device 210 further provides a first button (Learn more) that allows Bob to obtain additional information regarding the first recommendation and a second button (Schedule inspection) that allows Bob to schedule the visual inspection. Assume Bob selects the first button.

Figure 12C:
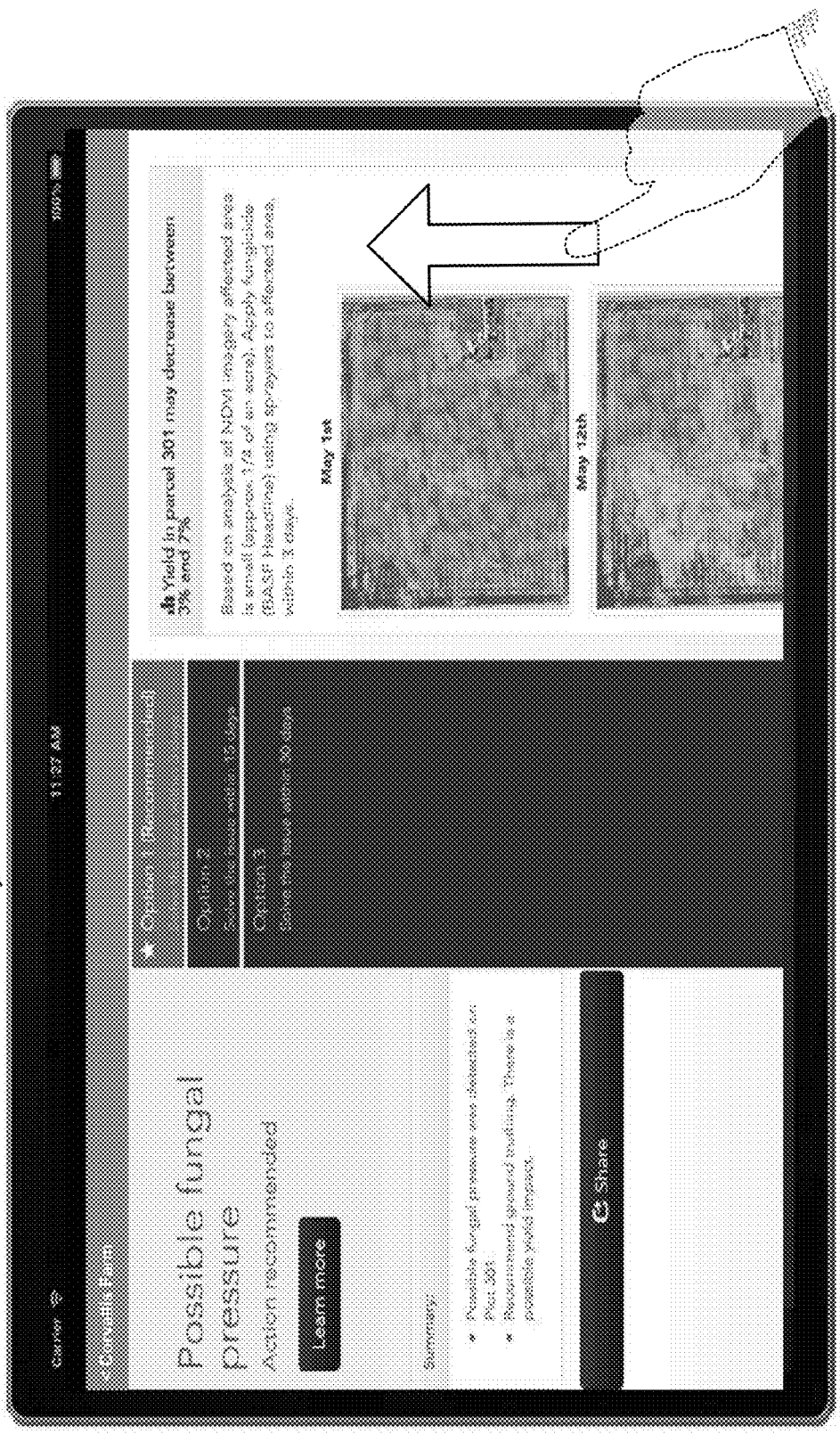
Figure 12D:
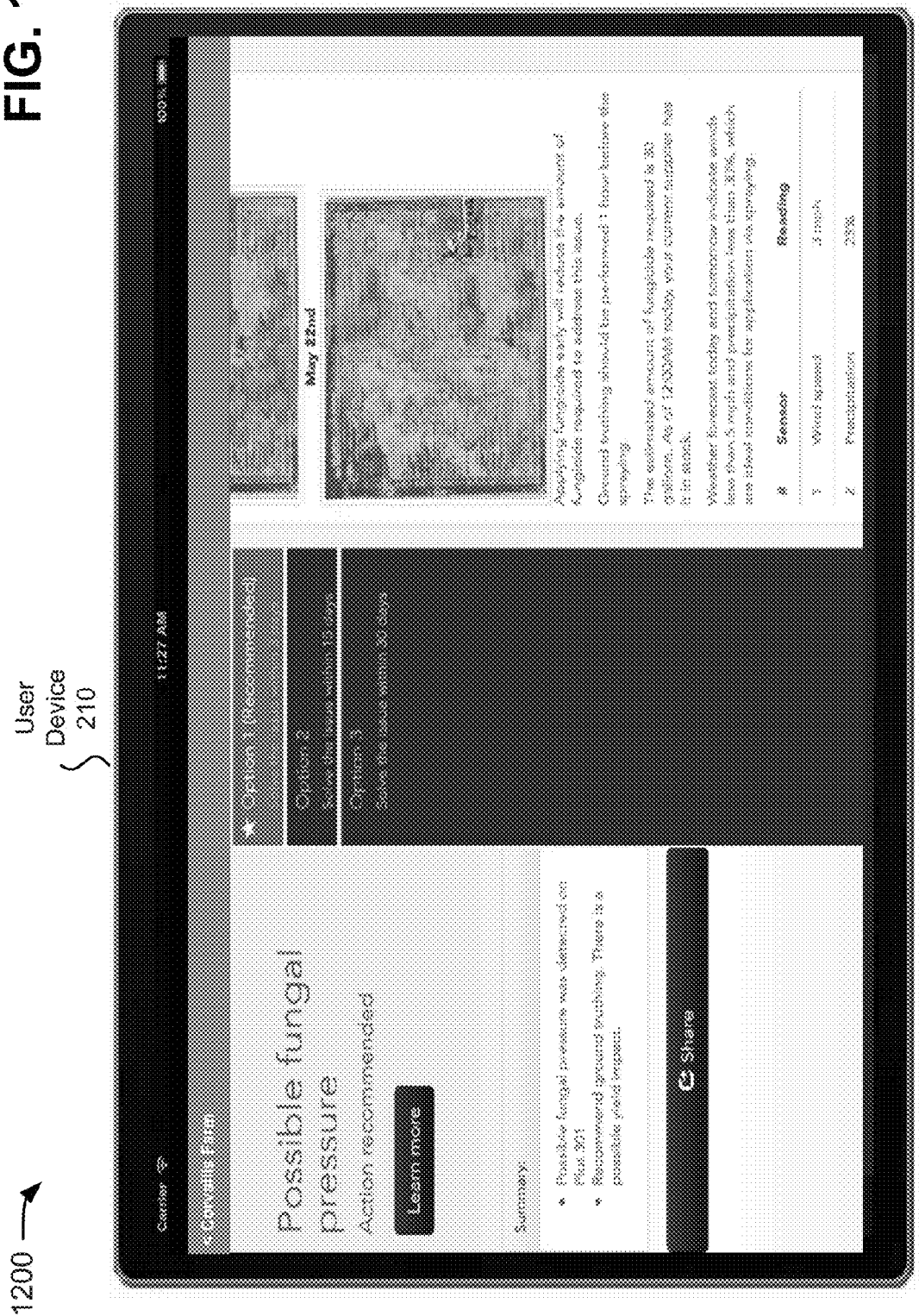

With reference to FIG. 12C, user device 210 displays additional detailed information relating to the alert. As shown, user device 210 displays NDVI imagery of plot 301 over time. As a result, Bob may view the NDVI imagery of plot 301 on May $1^{st}$ and May $12^{th}$. By scrolling down (as shown in FIG. 12C), Bob may also view the NDVI imagery of plot 301 on May $22^{nd}$, as shown in relation to FIG. 12D. By viewing the NDVI imagery of plot 301 over time, Bob may visually identify how the fungal pressure is worsening over time.

Figure 12E:
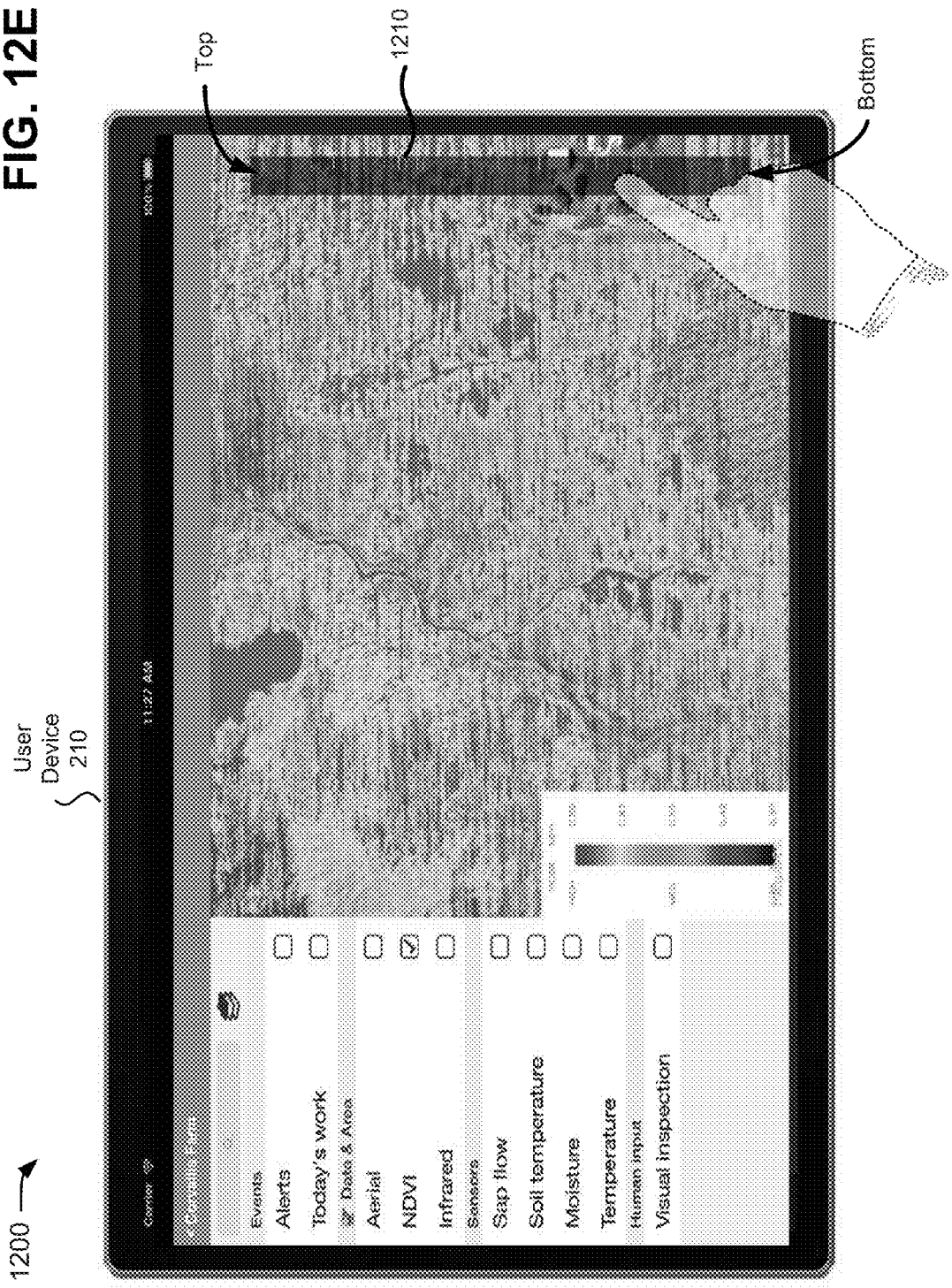

With reference to FIG. 12E, assume user device 210 provides NDVI imagery of plot 301 in additional detail. As shown, user device 210 provides a scroll bar 1210 that allows Bob to easily view the plot over time. The bottom of scroll bar 1210 corresponds to a future period of time. The top of scroll bar 1210 corresponds to a previous time period, which may be days earlier, weeks earlier, months earlier, or more than a year earlier than a current time period. In some implementations, scroll bar 1210 may be marked with dates. In some implementations, based on selection of scroll bar 1210, user device 210 may cause scroll bar 1210 to expand and display dates. Assume Bob selects scroll bar 1210 to cause scroll bar 1210 to expand and to cause dates to appear on scroll bar 1210.

Figure 12F:
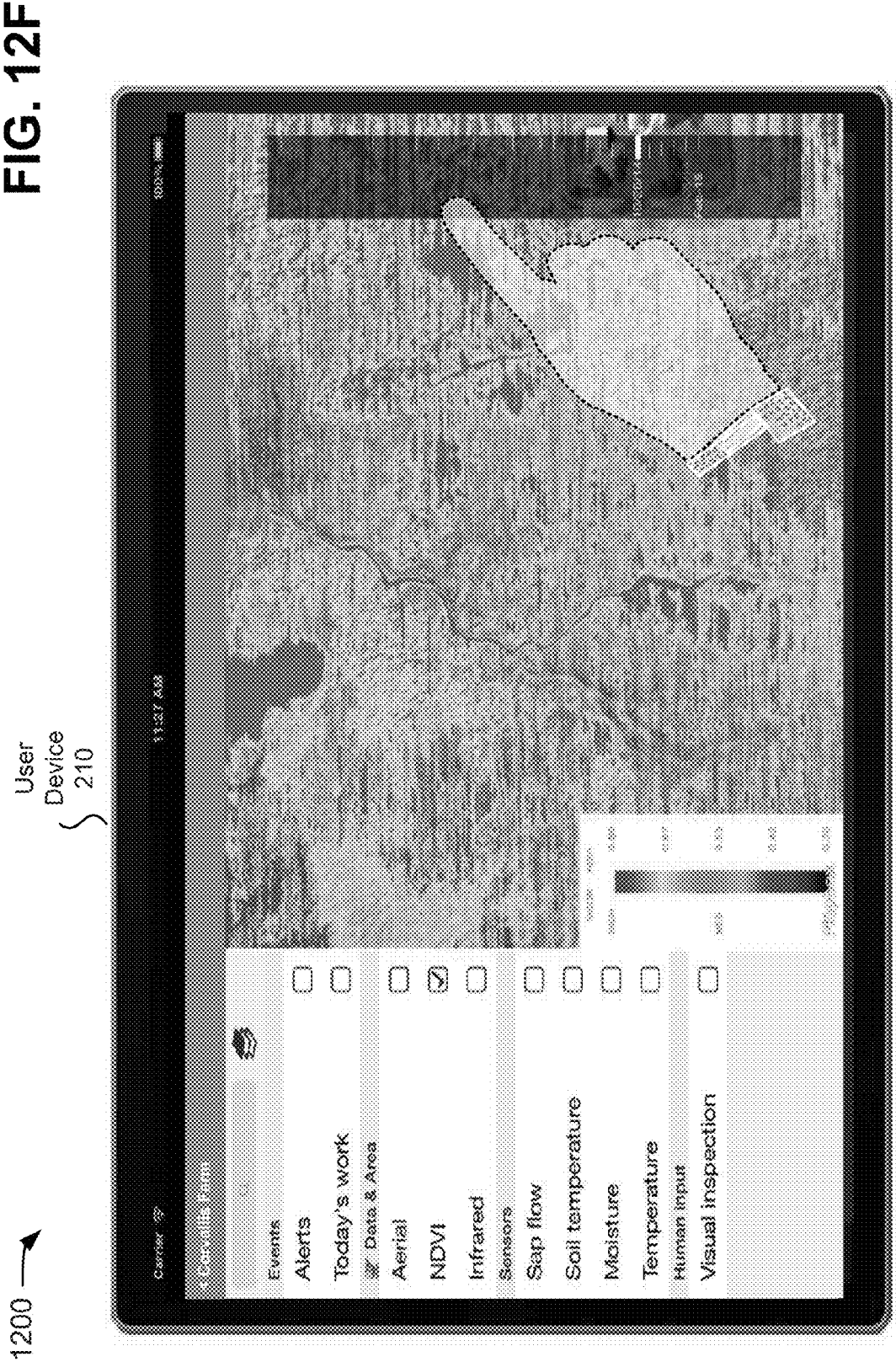
Figure 12G:
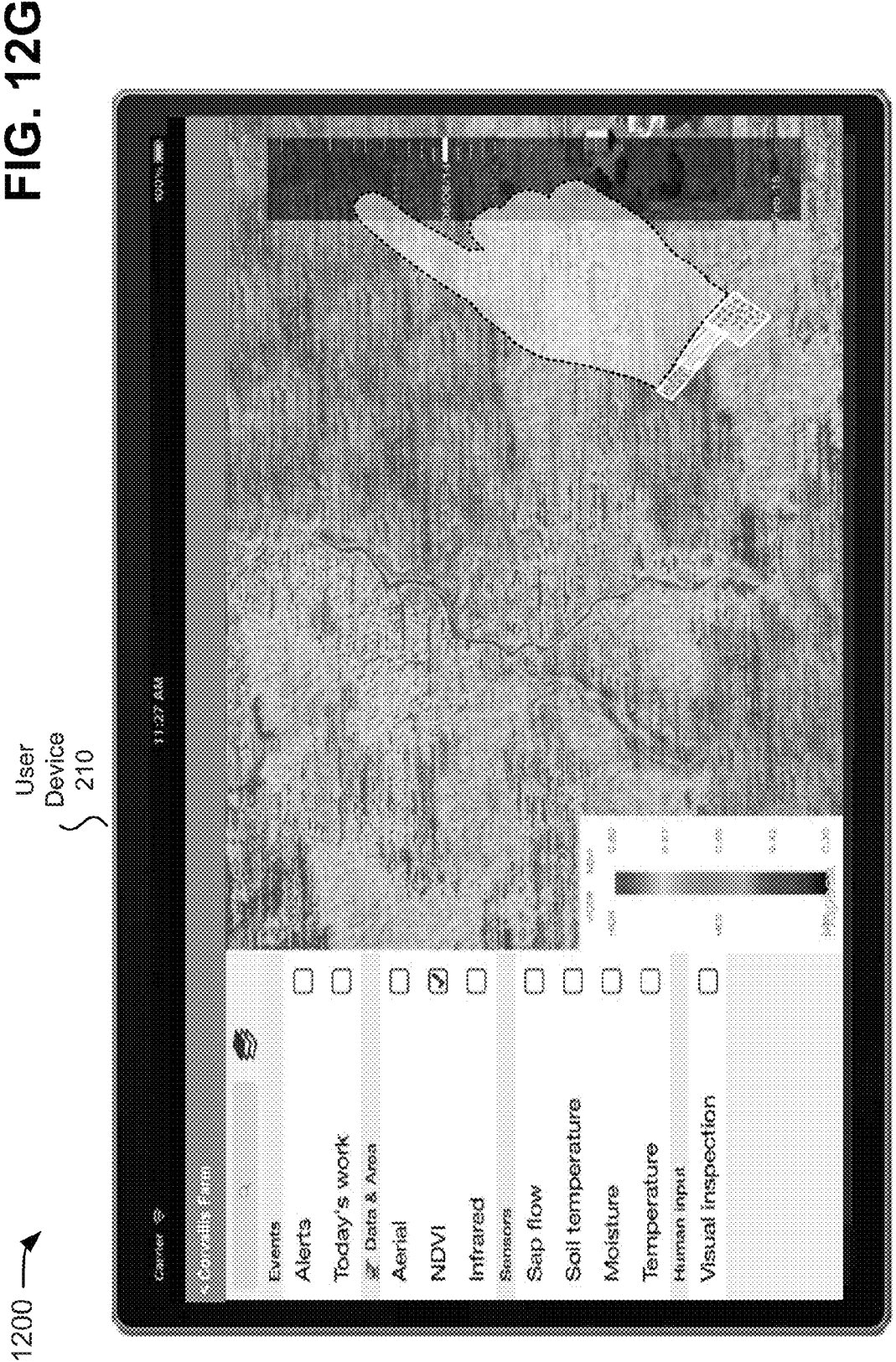
Figure 12H:
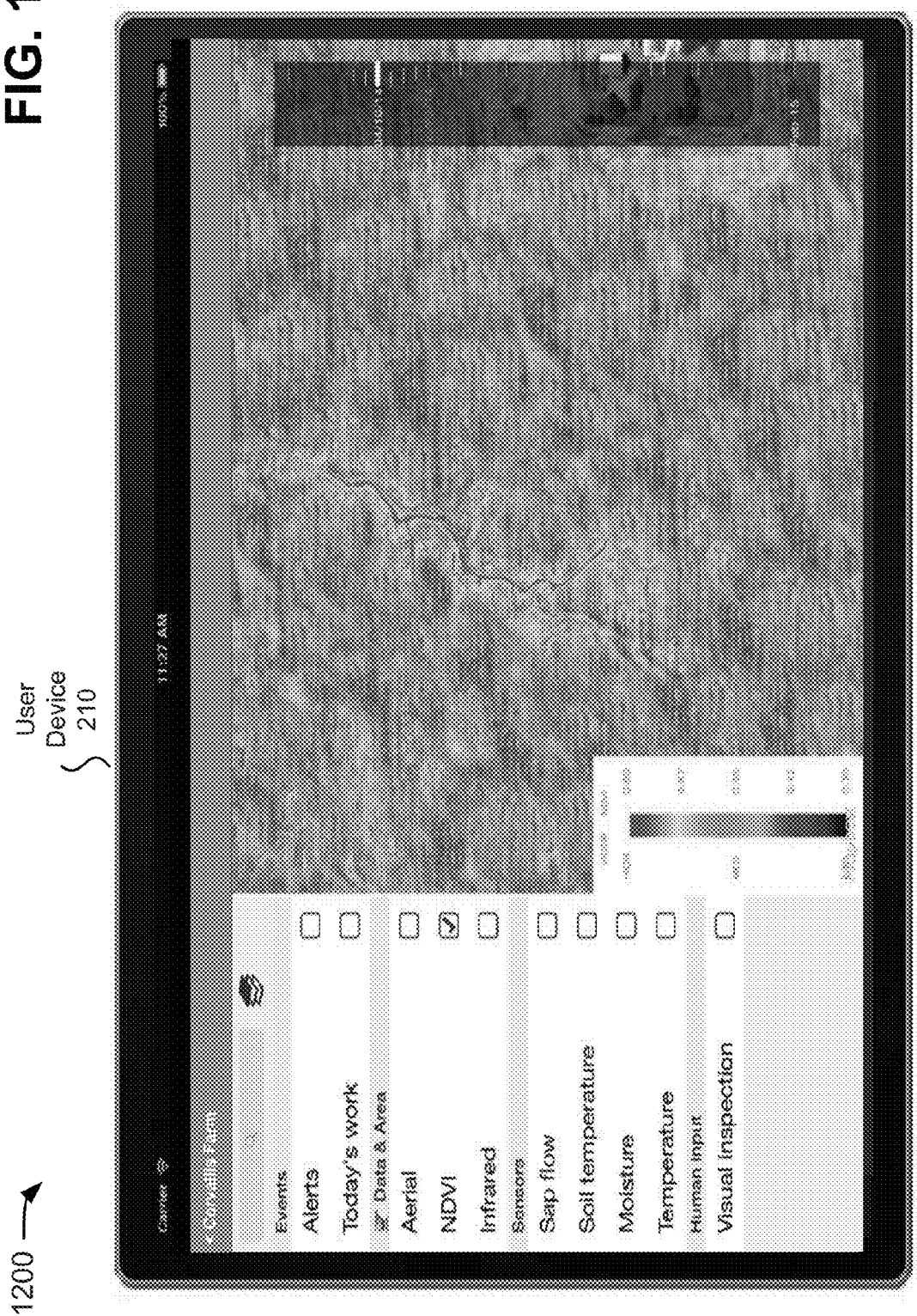

With reference to FIG. 12F, user device 210 may visually distinguish the date, of the displayed NDVI imagery, on scroll bar 1210. Assume that Bob continues to select earlier dates on scroll bar 1210, as shown in FIGS. 12G and 12H, to view NDVI imagery of plot 301 over time. In this way, a user may view a progression of images, that have been stitched together (e.g., in a timeline fashion), of a plot to determine how a particular issue has worsened or improved over time.

Figure 12I:
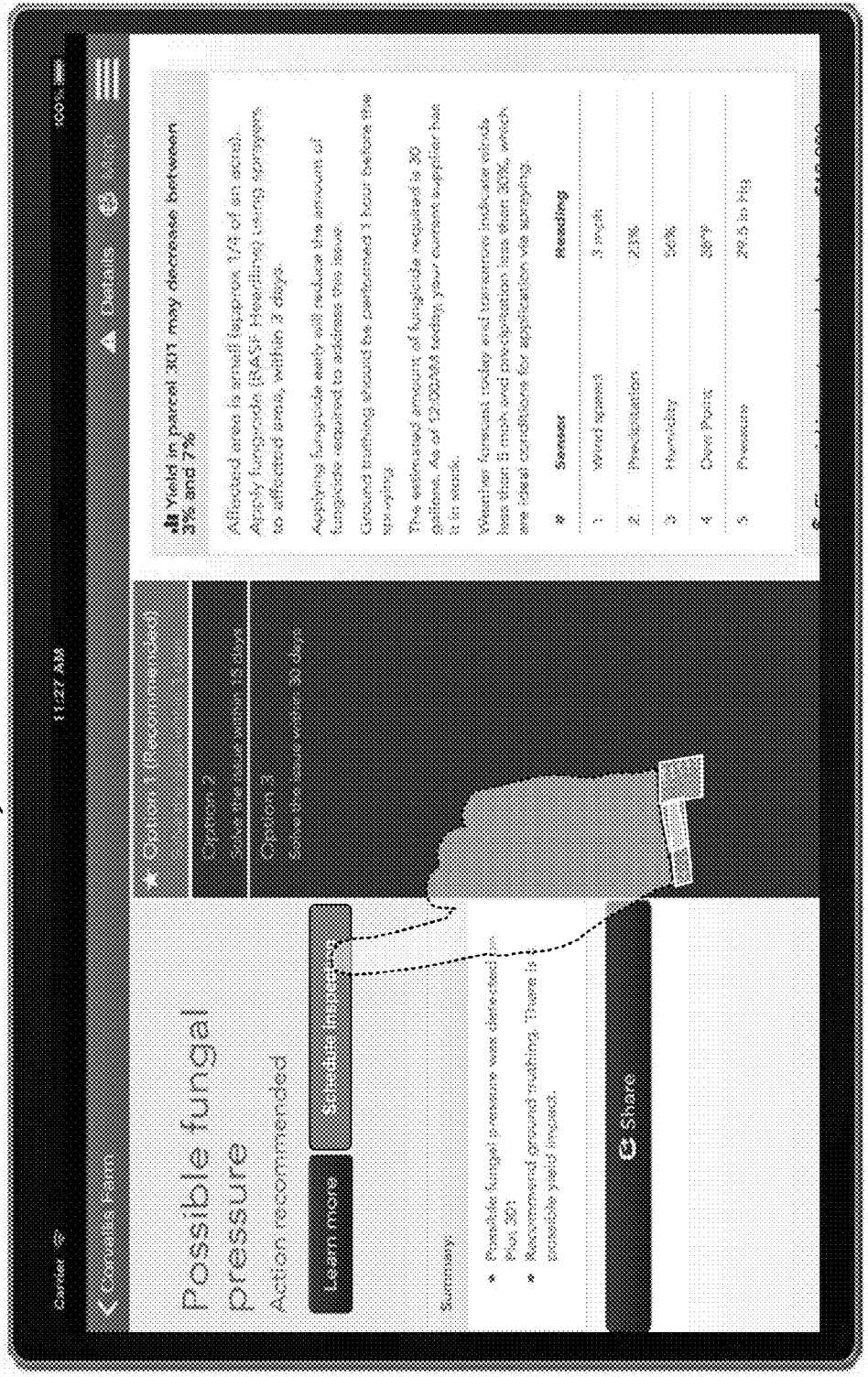

With reference to FIG. 12I, assume that user device 210, once again, provides the details regarding the fungal pressure issue, as described above with respect to FIG. 12B. In FIG. 12I, assume that Bob selects the second button (Schedule inspection) that allows Bob to schedule a visual inspection of plot 301.

With reference to FIG. 12J, user device 210 sends a visual inspection work order to precision agriculture system 250. The visual inspection work order identifies plot 301 and a date (or range of dates) on which the visual inspection is to occur. Based on receiving the visual inspection work order, precision agriculture system 250 may identify a worker (or manager) associated with plot 301 and send the visual inspection work order to a user device of the worker (or manager). Assume the visual inspection work order indicates that the worker is to visually inspect plot 301 for a possible fungal pressure issue. As a result, the worker may visually inspect plot 301. Once the visual inspection is complete, the worker may cause the user device to send a result of the visual inspection to precision agriculture system 250, which may include visual images of the plot. Precision agriculture system 250 may update one or more models based on the receiving result and provide updated information relating to the issue to user device 210.

Figure 12K:
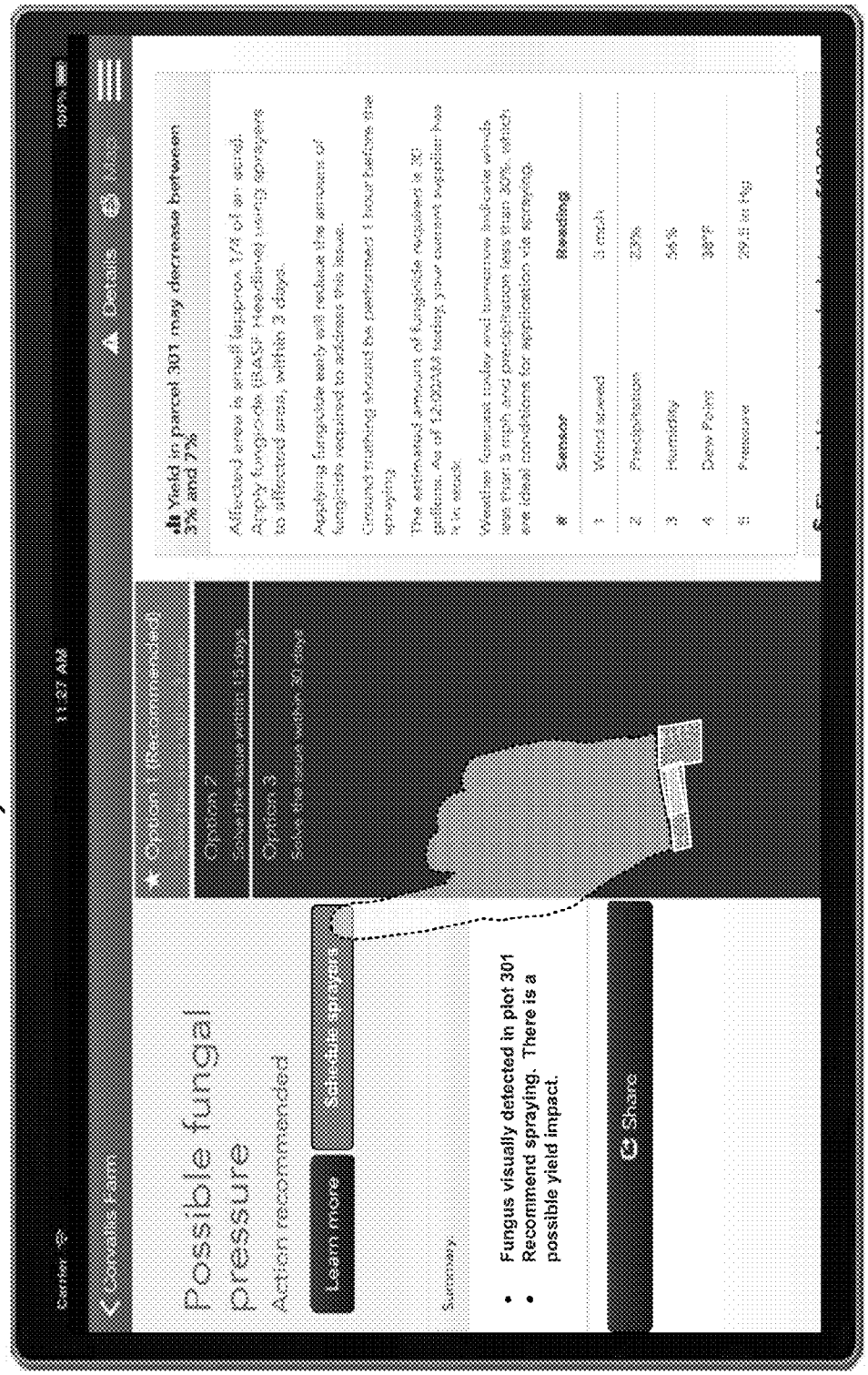

With reference to FIG. 12K, user device 210 displays detailed information relating to the visual inspection. As shown, user device 210 displays that fungus has been visually detected in plot 301 and that spraying of the plot is recommended. User device 210 now includes a button (Schedule sprayers) that allows Bob to schedule the spraying of plot 301 with the recommended amount of fungicide. Assume Bob selects the button.

Figure 12L:
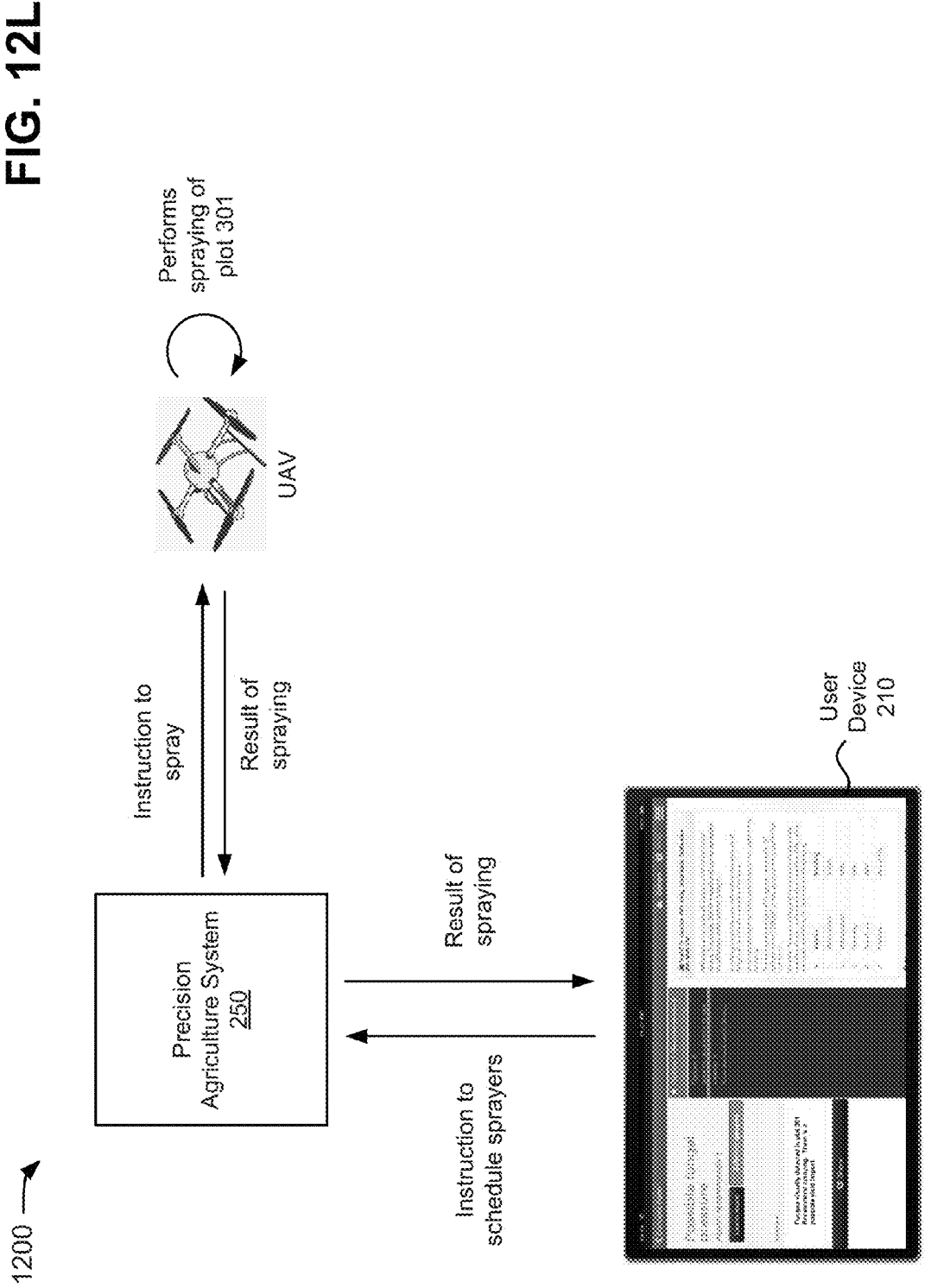

With reference to FIG. 12L, user device 210 sends an instruction, to precision agriculture system 250, to schedule the spraying of plot 301. The instruction identifies plot 301 and the amount of fungicide to spray. Based on receiving the instruction, precision agriculture system 250 may identify a farm device 260 (e.g., a UAV or a group of UAVs) to perform the spraying and how to communicate with farm device 260. Precision agriculture system 250 may cause farm device 260 to perform the spraying of plot 301. Once the spraying is complete, farm device 260 may send a notification of the completion of the spraying to precision agriculture system 250. Precision agriculture system 250 may update one or more models based on the notification and send a result of the spraying to user device 210.

As indicated above, FIGS. 12A-12L are provided merely as an example. Other examples are possible and may differ from what was described with regard to FIGS. 12A-12L.

Figure 13A:
Figure 13B:
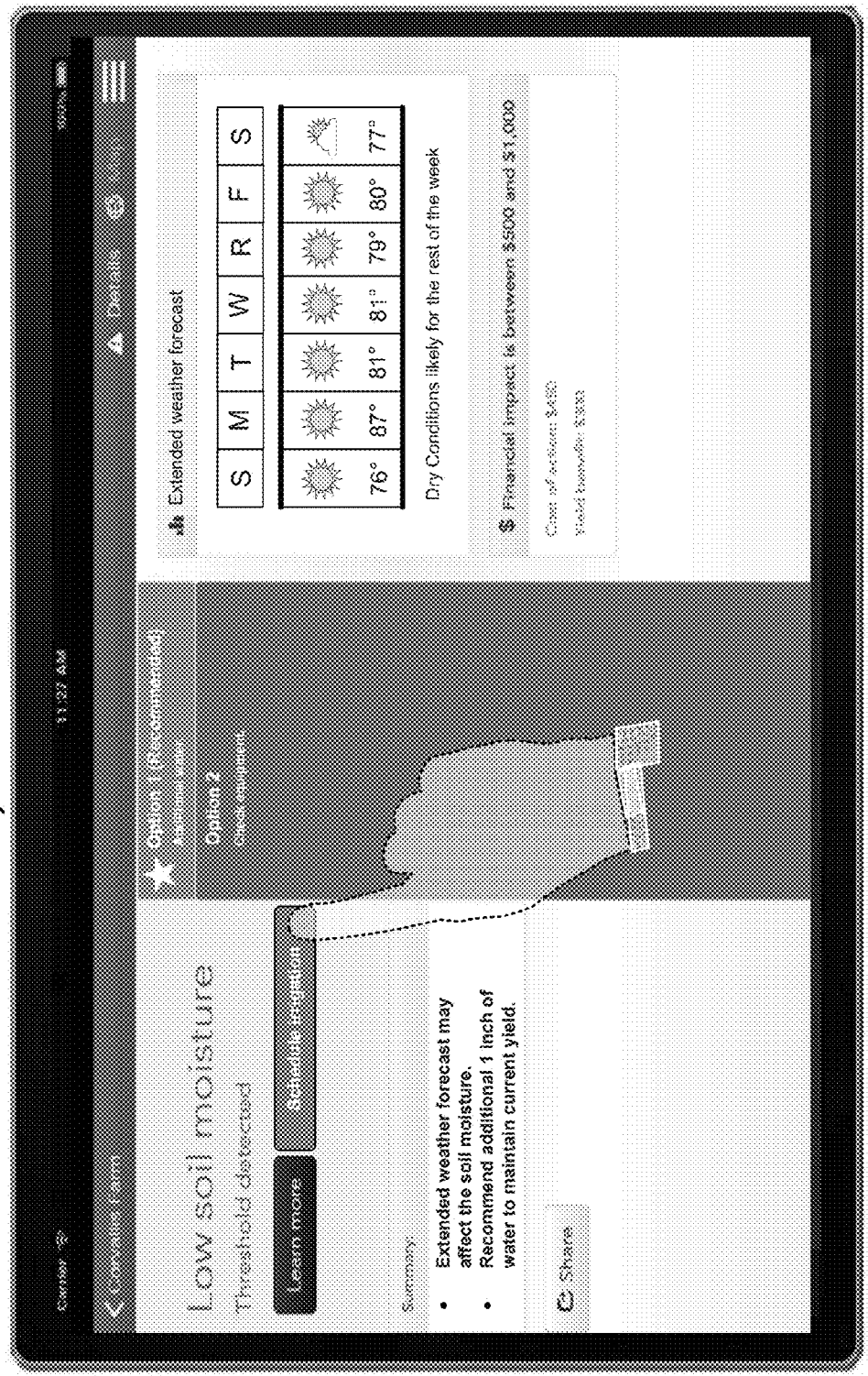

FIGS. 13A-13C are still another example 1300 of the process described above with respect to FIG. 7. With reference to FIG. 13A, assume, once again, that a user, named Bob Smith, has logged into the PAS application to obtain the precision agriculture service from precision agriculture system 250. In example 1300, assume that user device 210 provides an alert, in alert section 1305, relating to a possible low soil moisture issue at plot 101. Assume further that Bob selects the alert, as shown in FIG. 13A.

With reference to FIG. 13B, user device 210 displays detailed information relating to the alert. As shown, user device 210 displays two recommendations relating to the low soil moisture alert. The first recommendation relates to watering plot 101. The second recommendation relates to performing an inspection of the irrigation system associated with plot 101. User device 210 provides details relating to the first recommendation. As shown, by not watering plot 101, the financial impact may be a loss between $500 and $1,000. User device 210 further provides a first button (Learn more) that allows Bob to obtain additional information regarding the first recommendation and a second button (Schedule irrigation) that allows Bob to automatically water the plot. Assume Bob selects the second button.

With reference to FIG. 13C, user device 210 sends an instruction to turn on the irrigation system for a particular period of time to precision agriculture system 250. The instruction may include information identifying Bob, the irrigation system, and a period of time the irrigation system is to be turned on. Based on receiving the instruction, precision agriculture system 250 may identify a network address for the irrigation system and may cause the irrigation system to be turned on by sending an instruction to turn on to the irrigation system. Once the period of time has lapsed, precision agriculture system 250 may send an instruction to turn irrigation system off. Precision agriculture system 250 may update one or more models based on the watering of plot 101 being complete.

As indicated above, FIGS. 13A-13C are provided merely as an example. Other examples are possible and may differ from what was described with regard to FIGS. 13A-13C.

In this way, a precision agriculture system may provide recommended courses of action, to a farmer, that aid the farmer in running the day-to-day operations of a farm. By also providing financial impact information, the farmer may quickly realize the best course of action to take in a particular situation.

The foregoing disclosure provides illustration and description, but is not intended to be exhaustive or to limit the implementations to the precise form disclosed. Modifications and variations are possible in light of the above disclosure or may be acquired from practice of the implementations.

As used herein, the term component is intended to be broadly construed as hardware, firmware, and/or a combination of hardware and software.

Certain user interfaces have been described herein and/or shown in the figures. A user interface may include a graphical user interface, a non-graphical user interface, a text-based user interface, etc. A user interface may provide information for display. In some implementations, a user may interact with the information, such as by providing input via an input component of a device that provides the user interface for display. In some implementations, a user interface may be configurable by a device and/or a user (e.g., a user may change the size of the user interface, information provided via the user interface, a position of information provided via the user interface, etc.). Additionally, or alternatively, a user interface may be pre-configured to a standard configuration, a specific configuration based on a type of device on which the user interface is displayed, and/or a set of configurations based on capabilities and/or specifications associated with a device on which the user interface is displayed.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware can be designed to implement the systems and/or methods based on the description herein.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the terms "set" and "group" are intended to include one or more items (e.g., related items, unrelated items, or the like), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A method, comprising:
   capturing, by a processor of a first device, from a plurality of sensors, and via a network, first data regarding one or more farms,
   the plurality of sensors including:

a ground-based sensor, and
an aerial-based sensor,
the first data including:
ground-related data provided by the ground-based sensor, and aerial-related data provided by the aerial-based sensor;
receiving, by the processor, from a plurality of sources, and via the network, second data regarding the one or more farms,
the plurality of sources being different than the plurality of sensors,
the second data being different than the first data, and
the second data including at least one of:
imagery data, or
numeric data;
processing, by the processor, the first data to create processed first data;
processing, by the processor, the second data to create processed second data;
creating, by the processor, a model,
the model being created using a machine learning technique, the processed first data, and the processed second data;
training, by the processor, the model based on training data,
the training data including:
information relating to an action taken, and
information identifying a result of taking the action;
receiving, by the processor and via the network, sensor data associated with a geographic location;
determining, by the processor and using the model and the sensor data, a recommended course of action in relation to a plot of the one or more farms,
the recommended course of action including gathering additional data regarding the plot;
providing, by the processor and for display, a map that visually identifies an alert relating to the plot,
the alert indicating that a potential issue exists regarding the plot or information regarding harvesting the plot;
receiving, by the processor, a selection of the alert;
providing, by the processor and for display, information identifying the recommended course of action based on receiving the selection of the alert;
receiving, by the processor, a selection relating to the recommended course of action; and
causing, by the processor and based on receiving the selection relating to the recommended course of action, a second device, associated with the geographic location, to perform the recommended course of action,
the second device being an unmanned aerial vehicle, and
the second device being different than the first device.

2. The method of claim 1,
where the geographic location is the plot,
where the gathering of the additional data includes capturing an image of the plot, and
where, when causing the second device to perform the recommended course of action, the method includes:
causing the unmanned aerial vehicle to capture the image of the plot.

3. The method of claim 1,
where the geographic location is the plot, and
where, when creating the model, the method includes:
creating a plurality of models for the plot,
the plurality of models including:
a first model that is associated with a first portion of the plot, and
a second model that is different than the first model and that is associated with a second portion of the plot,
the first portion and the second portion corresponding to different portions of the plot or different crops of the plot.

4. The method of claim 1, further comprising:
causing the second device or a third device, associated with the geographic location, to perform a different course of action,
where at least one of the recommended course of action or the different course of action relates to at least one of:
maintenance of a piece of farming equipment associated with the plot,
the plot relating to the geographic location,
malfunction of the piece of farming equipment associated with the plot,
harvest of a crop associated with the plot,
storage of the crop associated with the plot,
sale of the crop associated with the plot,
detection of a disease in the plot,
detection of an insect issue in connection with the plot, or
an irrigation issue of the plot.

5. The method of claim 1,
where, when determining the recommended course of action, the method includes:
determining a plurality of recommended courses of action;
determining, for each recommended course of action of the plurality of recommended courses of action, an impact of performing the recommended course of action or not performing the recommended course of action; and
ranking the plurality of recommended courses of action, based on determining the impact for each recommended course of action, to create a ranked list; and
where, when providing the information identifying the recommended course of action, the method includes:
providing information identifying the ranked list to a user device.

6. The method of claim 1, further comprising:
causing a third device, associated with the geographic location, to perform a different course of action,
where the geographic location is the plot,
where the third device includes an irrigation system,
where the different course of action relates to watering of the plot, and
where, when causing the third device to perform the different course of action, the method includes:
causing the irrigation system to water the plot for a particular period of time.

7. The method of claim 1,
where the recommended course of action relates to an issue in connection with the plot, and
where the method further comprises:
providing, for display, a user interface,
the user interface including:
aerial imagery of the plot at a point in time, and
an interface that allows aerial imagery of the plot to be viewed at different points in time.

8. A non-transitory computer-readable medium storing instructions, the instructions comprising:

a plurality of instructions, which, when executed by a processor of a first device, cause the processor to:
 capture, from a plurality of sensors and via a network, first data regarding one or more farms,
  the plurality of sensors including:
   a ground-based sensor, and
   an aerial-based sensor,
  the first data including:
   ground-related data provided by the ground-based sensor, and
   aerial-related data provided by the aerial-based sensor;
 receive, from a plurality of sources and via the network, second data regarding the one or more farms,
  the plurality of sources being different than the plurality of sensors,
  the second data being different than the first data, and
  the second data including at least one of:
   imagery data, or
   numeric data;
 process the first data to create processed first data;
 process the second data to create processed second data;
 create a model,
  the model being created using a machine learning technique,
  the processed first data, and the processed second data;
 receive, via the network, sensor data associated with a geographic location;
 determine, using the model and the sensor data, a recommended course of action in relation to a plot of the one or more farms,
  the recommended course of action including gathering additional data regarding the plot;
 provide, for display, a map that visually identifies an alert relating to the plot,
  the alert indicating that a potential issue exists regarding the plot or information regarding harvesting the plot;
 receive a selection of the alert;
 provide, for display, information identifying the recommended course of action based on receiving the selection of the alert;
 receive a selection relating to the recommended course of action; and
 cause, based on receiving the selection relating to the recommended course of action, a second device, associated with the geographic location, to perform the recommended course of action,
  the second device being an unmanned aerial vehicle, and
  the second device being different than the first device.

9. The non-transitory computer-readable medium of claim 8,
 where the geographic location is the plot,
 where the gathering of the additional data includes capturing an image of the plot, and
 where the plurality of instructions, that cause the processor to cause the second device to perform the recommended course of action, cause the processor to:
  cause the unmanned aerial vehicle to capture the image of the plot.

10. The non-transitory computer-readable medium of claim 8,
 where the geographic location is the plot, and where the plurality of instructions, that cause the processor to create the model, cause the processor to:
  create a plurality of models for the plot,
   the plurality of models including:
    a first model,
     the first model being associated with a first portion of the plot, and
    a second model,
     the second model being different than the first model,
     the second model being associated with a second portion of the plot, and
     the first portion and the second portion corresponding to different crops of the plot or different portions of the plot.

11. The non-transitory computer-readable medium of claim 8,
 where the geographic location is the plot,
 where the sensor data is associated with the plot,
 where the recommended course of action relates to an insect infestation or a disease, and
 where the plurality of instructions, when executed by the processor, further cause the processor to:
  provide a set of images of the plot,
   the set of images providing a timeline of an effect of the insect infestation or the disease on the plot over time.

12. The non-transitory computer-readable medium of claim 8,
 where the plurality of instructions, when executed by the processor, further cause the processor to:
  cause the second device or a third device, associated with the geographic location, to perform a different course of action,
 where the geographic location is the plot, and
 where at least one of the recommended course of action or the different course of action relates to at least one of:
  maintenance of a piece of farming equipment associated with the plot,
  malfunction of the piece of farming equipment associated with the plot,
  harvest of a crop associated with the plot,
  storage of the crop associated with the plot,
  sale of the crop associated with the plot,
  detection of a disease in the plot,
  detection of an insect issue in connection with the plot, or
  an irrigation issue of the plot.

13. The non-transitory computer-readable medium of claim 8, where the plurality of instructions, that cause the processor to determine the recommended course of action, cause the processor to:
 determine a plurality of recommended courses of action;
 determine, for each recommended course of action of the plurality of recommended courses of action, an impact of performing the recommended course of action or not performing the recommended course of action;
 order the plurality of recommended courses of action, based on determining the impact for each recommended course of action, to create an ordered list; and
 where the plurality of instructions, that cause the processor to provide the information identifying the recommended course of action, cause the processor to:
  provide the ordered list.

14. The non-transitory computer-readable medium of claim 8, where the recommended course of action relates to an issue in connection with the plot, and
where the plurality of instructions, when executed by the processor, further cause the processor to:
provide, for display, a user interface,
the user interface including:
aerial imagery of the plot at a point in time, and
an interface that allows aerial imagery of the plot to be viewed at different points in time.

15. A first device, comprising:
a memory to store instructions; and
a processor to execute the instructions to:
capture, from a plurality of sensors and via a network, first data regarding one or more farms,
the plurality of sensors including:
a ground-based sensor, and
an aerial-based sensor,
the first data including:
ground-related data provided by the ground-based sensor, and
aerial-related data provided by the aerial-based sensor;
receive, from a plurality of sources and via the network, second data regarding the one or more farms,
the plurality of sources being different than the plurality of sensors,
the second data being different than the first data, and
the second data including at least one of:
imagery data, or
numeric data;
process the first data to create processed first data;
process the second data to create processed second data;
create a model,
the model being created using a machine learning technique, the processed first data, and the processed second data;
receive, via the network, sensor data associated with a geographic location;
determine, using the model and the sensor data, a recommended course of action in relation to a plot of the one or more farms,
the recommended course of action including gathering additional data regarding the plot;
provide, for display, a map that visually identifies an alert relating to the plot,
the alert indicating that a potential issue exists regarding the plot or information regarding harvesting the plot;
receive a selection of the alert;
provide, for display, information identifying the recommended course of action based on receiving the selection of the alert;
receive a selection relating to the recommended course of action; and
cause, based on receiving the selection relating to the recommended course of action, a second device, associated with the geographic location, to perform the recommended course of action,
the second device being an unmanned aerial vehicle, and
the second device being different than the first device.

16. The first device of claim 15,
where the geographic location is the plot, and
where the processor is further to:
cause the unmanned aerial vehicle to spray the plot.

17. The first device of claim 15, where, when determining the recommended course of action, the processor is to:
determine an impact of performing the recommended course of action or not performing the recommended course of action, and
provide, for display, information identifying the impact of performing the recommended course of action or not performing the recommended course of action.

18. The first device of claim 15,
where the geographic location is the plot, and
where, when creating the model, the processor is to:
create a plurality of models for the plot,
the plurality of models including:
a first model,
the first model being associated with a first portion of the plot, and
a second model,
the second model being different than the first model,
the second model being associated with a second portion of the plot, and
the first portion and the second portion corresponding to different crops of the plot or different portions of the plot.

19. The first device of claim 15,
where the recommended course of action relates to harvesting, storing, or selling a crop associated with the plot, and
where the processor is further to:
determine a peak price time period, during a period of time, for the crop,
determine a growth degree days maturity time period, during a calendar year, for the crop,
determine a peak price harvest period, during the period of time, based on the peak price time period and the growth degree days maturity time period,
determine a peak yield time period, during the period of time, for the crop,
predict a yield gross, for a period during the period of time, based on the peak price harvest period and the peak yield time period,
determine financial information based on the predicted yield gross, and
provide, for display, the financial information.

20. The first device of claim 15, where, when determining the recommended course of action, the processor is to:
determine a plurality of recommended courses of action,
determine, for each recommended course of action of the plurality of recommended courses of action, an impact of performing the recommended course of action or not performing the recommended course of action,
order the plurality of recommended courses of action, based on determining the impact for each recommended course of action, to create an ordered list, and
where, when providing the information identifying the recommended course of action, the processor is to:
provide the ordered list.

\* \* \* \* \*